United States Patent
Shelton, IV et al.

(10) Patent No.: US 12,279,769 B1
(45) Date of Patent: Apr. 22, 2025

(54) STAPLE CARTRIDGE COMPRISING A SLED HAVING A DRIVER LIFT CAM

(71) Applicant: Cilag GmbH International, Zug (CH)

(72) Inventors: Frederick E. Shelton, IV, Hillsboro, OH (US); Jason L. Harris, Lebanon, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/379,805

(22) Filed: Oct. 13, 2023

(51) Int. Cl.
 *A61B 17/072* (2006.01)
 *A61B 17/00* (2006.01)

(52) U.S. Cl.
 CPC .. *A61B 17/072* (2013.01); *A61B 2017/00367* (2013.01); *A61B 2017/07271* (2013.01); *A61B 2017/07278* (2013.01); *A61B 2017/07285* (2013.01)

(58) Field of Classification Search
 CPC ........ A61B 17/072; A61B 2017/00367; A61B 2017/07271; A61B 2017/07278; A61B 2017/07285
 See application file for complete search history.

(56) References Cited

U.S. PATENT DOCUMENTS

| | | | |
|---|---|---|---|
| 5,403,312 A | 4/1995 | Yates et al. | |
| 5,485,947 A | 1/1996 | Olson et al. | |
| 6,978,921 B2 | 12/2005 | Shelton, IV et al. | |
| 7,000,818 B2 | 2/2006 | Shelton, IV et al. | |
| 7,401,721 B2 | 7/2008 | Holsten et al. | |
| 7,407,075 B2 | 8/2008 | Holsten et al. | |
| 7,422,139 B2 | 9/2008 | Shelton, IV et al. | |
| 7,464,849 B2 | 12/2008 | Shelton, IV et al. | |
| 7,669,746 B2 | 3/2010 | Shelton, IV et al. | |
| 7,670,334 B2 | 3/2010 | Hueil et al. | |
| 7,735,703 B2 | 6/2010 | Morgan et al. | |

(Continued)

FOREIGN PATENT DOCUMENTS

| | | |
|---|---|---|
| CN | 105919642 A | 9/2016 |
| CN | 105997172 A | 10/2016 |

(Continued)

OTHER PUBLICATIONS

U.S. Food and Drug Administration 510(k) Premarket Notification, https://www.accessdata.fda.gov/scripts/cdrh/ofdocs/cfpmn/omn.cfm?ID=K182476, last update: Jan. 8, 2024, 1 page.

(Continued)

*Primary Examiner* — Michelle Lopez

(57) ABSTRACT

A staple cartridge for use with a surgical instrument, the staple cartridge comprising a cartridge body, a staple, a staple driver, and a sled is disclosed. The sled is movable from a proximal position to a distal position during a firing stroke and is movable from the distal position toward the proximal position during a retraction stroke. The sled comprises a first rail comprising a first distal-facing ramp, a second rail comprising a second distal-facing ramp, and a driver lift cam positioned intermediate the first rail and the second rail. The first distal-facing ramp and the second distal-facing ramp are configured to engage and move the staple driver from an unfired position to a fired position during the firing stroke. The driver lift cam is configured to engage the staple driver and move the staple driver toward the fired position during the retraction stroke.

20 Claims, 15 Drawing Sheets

(56) References Cited

U.S. PATENT DOCUMENTS

| | | |
|---|---|---|
| 7,753,245 B2 | 7/2010 | Boudreaux et al. |
| 7,845,537 B2 | 12/2010 | Shelton, IV et al. |
| 7,980,443 B2 | 7/2011 | Scheib et al. |
| 8,123,100 B2 | 2/2012 | Holsten et al. |
| 8,141,762 B2 | 3/2012 | Bedi et al. |
| 8,210,411 B2 | 7/2012 | Yates et al. |
| 8,220,688 B2 | 7/2012 | Laurent et al. |
| 8,308,040 B2 | 11/2012 | Huang et al. |
| 8,393,514 B2 | 3/2013 | Shelton, IV et al. |
| 8,499,992 B2 | 8/2013 | Whitman et al. |
| 8,540,133 B2 | 9/2013 | Bedi et al. |
| 8,561,870 B2 | 10/2013 | Baxter, III et al. |
| 8,608,045 B2 | 12/2013 | Smith et al. |
| 8,733,613 B2 | 5/2014 | Huitema et al. |
| 8,864,007 B2 | 10/2014 | Widenhouse et al. |
| 8,876,857 B2 | 11/2014 | Burbank |
| 9,050,083 B2 | 6/2015 | Yates et al. |
| 9,072,535 B2 | 7/2015 | Shelton, IV et al. |
| 9,101,358 B2 | 8/2015 | Kerr et al. |
| 9,131,940 B2 | 9/2015 | Huitema et al. |
| 9,345,481 B2 | 5/2016 | Hall et al. |
| 9,386,988 B2 | 7/2016 | Baxter, III et al. |
| 9,629,631 B2 | 4/2017 | Nicholas et al. |
| 9,770,245 B2 | 9/2017 | Swayze et al. |
| 9,788,835 B2 | 10/2017 | Morgan et al. |
| 9,839,420 B2 | 12/2017 | Shelton, IV et al. |
| 9,844,369 B2 | 12/2017 | Huitema et al. |
| 9,924,944 B2 | 3/2018 | Shelton, IV et al. |
| 9,987,008 B2 | 6/2018 | Scirica et al. |
| 10,080,552 B2 | 9/2018 | Nicholas et al. |
| 10,085,749 B2 | 10/2018 | Cappola et al. |
| 10,105,142 B2 | 10/2018 | Baxter, III et al. |
| 10,123,798 B2 | 11/2018 | Baxter, III et al. |
| 10,130,363 B2 | 11/2018 | Huitema et al. |
| 10,166,023 B2 | 1/2019 | Vendely et al. |
| 10,213,203 B2 | 2/2019 | Swayze et al. |
| 10,299,792 B2 | 5/2019 | Huitema et al. |
| 10,349,939 B2 | 7/2019 | Shelton, IV et al. |
| 10,357,252 B2 | 7/2019 | Harris et al. |
| 10,517,593 B2 | 12/2019 | Gupta et al. |
| 10,537,324 B2 | 1/2020 | Shelton, IV et al. |
| 10,542,981 B2 | 1/2020 | Miller et al. |
| 10,561,419 B2 | 2/2020 | Beardsley |
| 10,568,624 B2 | 2/2020 | Shelton, IV et al. |
| 10,588,623 B2 | 3/2020 | Schmid et al. |
| 10,765,427 B2 | 9/2020 | Shelton, IV et al. |
| 10,898,183 B2 | 1/2021 | Shelton, IV et al. |
| 10,898,191 B2 | 1/2021 | Huitema et al. |
| 10,945,727 B2 | 3/2021 | Shelton, IV et al. |
| 10,952,724 B2 | 3/2021 | Shelton, IV et al. |
| 11,000,278 B2 | 5/2021 | Shelton, IV et al. |
| 11,045,191 B2 | 6/2021 | Shelton, IV et al. |
| 11,058,426 B2 | 7/2021 | Nalagatla et al. |
| D933,220 S | 10/2021 | Tate et al. |
| 11,147,552 B2 | 10/2021 | Burbank et al. |
| 11,207,065 B2 | 12/2021 | Harris et al. |
| 11,229,433 B2 | 1/2022 | Schings et al. |
| 11,234,698 B2 | 2/2022 | Shelton, IV et al. |
| 11,234,700 B2 | 2/2022 | Ragosta et al. |
| 11,291,445 B2 | 4/2022 | Shelton, IV et al. |
| 11,298,129 B2 | 4/2022 | Bakos et al. |
| 11,337,693 B2 | 5/2022 | Hess et al. |
| 11,364,029 B2 | 6/2022 | Burbank et al. |
| 11,382,627 B2 | 7/2022 | Huitema et al. |
| D967,421 S | 10/2022 | Shelton, IV et al. |
| 11,490,890 B2 | 11/2022 | Harris et al. |
| 11,517,315 B2 | 12/2022 | Huitema et al. |
| D974,560 S | 1/2023 | Shelton, IV et al. |
| 11,540,826 B2 | 1/2023 | Nalagatla et al. |
| 11,571,213 B2 | 2/2023 | Huitema et al. |
| 11,589,865 B2 | 2/2023 | Shelton, IV et al. |
| 11,701,114 B2 | 7/2023 | Shelton, IV et al. |
| 11,737,752 B2 | 8/2023 | Schings et al. |
| 11,766,257 B2 | 9/2023 | Shelton, IV et al. |
| 11,826,047 B2 | 11/2023 | Huang et al. |
| 11,849,944 B2 | 12/2023 | Shelton, IV et al. |
| 11,896,218 B2 | 2/2024 | Bakos et al. |
| 11,974,741 B2 | 5/2024 | Moubarak et al. |
| 2007/0175955 A1 | 8/2007 | Shelton et al. |
| 2014/0001231 A1 | 1/2014 | Shelton, IV et al. |
| 2014/0263552 A1 | 9/2014 | Hall et al. |
| 2015/0134077 A1 | 5/2015 | Shelton, IV et al. |
| 2018/0132849 A1 | 5/2018 | Miller et al. |
| 2018/0168615 A1 | 6/2018 | Shelton, IV et al. |
| 2019/0105047 A1 | 4/2019 | Nalagatla et al. |
| 2021/0186502 A1* | 6/2021 | Shelton, IV ..... A61B 17/07207 |
| 2022/0031320 A1 | 2/2022 | Hall et al. |
| 2022/0031351 A1 | 2/2022 | Moubarak et al. |
| 2022/0047265 A1 | 2/2022 | Miller et al. |
| 2022/0304679 A1 | 9/2022 | Bakos et al. |
| 2022/0346858 A1 | 11/2022 | Aronhalt et al. |
| 2023/0119119 A1 | 4/2023 | Moubarak |

FOREIGN PATENT DOCUMENTS

| | | |
|---|---|---|
| CN | 105997173 A | 10/2016 |
| CN | 106036848 A | 10/2016 |
| CN | 108542454 A | 9/2018 |
| CN | 111195142 A | 5/2020 |

OTHER PUBLICATIONS

U.S. Appl. No. 12/031,573, filed Feb. 14, 2008.

* cited by examiner

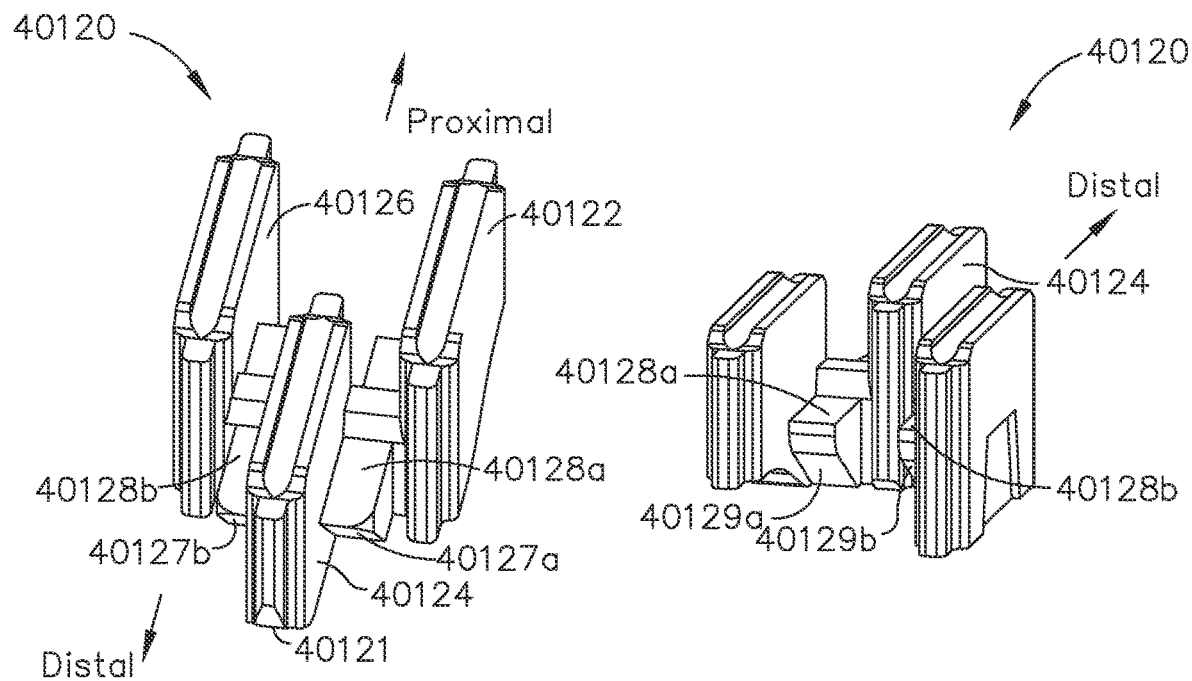
FIG. 9
FIG. 10
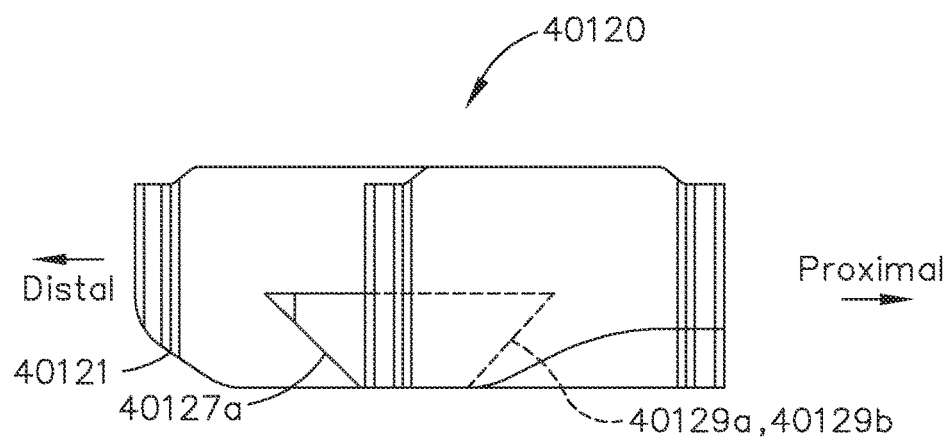
FIG. 11

STAPLE CARTRIDGE COMPRISING A SLED HAVING A DRIVER LIFT CAM

BACKGROUND

The present invention relates to surgical instruments and, in various arrangements, to surgical stapling and cutting instruments, end effectors, and staple cartridges for use therewith that are designed to staple and cut tissue.

Various surgical instrument assemblies are configured to fire staple cartridges having a sled that is configured to cammingly engage staple drivers positioned in the staple cartridge to eject staples removably stored in the staple cartridge during a staple firing stroke. The staple drivers are movably positioned within staple cavities in the staple cartridge and are movable from unfired positions to fired positions by the sled to eject the staples. The staple drivers can remain in their fired positions after the sled passes by due to the staple drivers being closely fit within their respective staple cavities. However, the staple drivers may drop, or fall, into or toward their unfired positions after the sled passes by. Absent more, the staple drivers may block the return path of the sled and prevent the sled from being retracted after the staple firing stroke. Moreover, the sled may also have a tissue cutting knife, such that the tissue cutting knife can remain exposed to the patient tissue when the sled is stuck in an advanced position. Various sled and firing driver arrangements disclosed herein address such problems without employing arrangements that are generally longer than conventional sled and firing driver configurations which might otherwise lead to longer end effector lengths.

SUMMARY

In accordance with the present disclosure, a staple cartridge for use with a surgical instrument is disclosed. The staple cartridge comprises a cartridge body, a staple, a staple driver, and a sled. The cartridge body comprises a deck, a longitudinal slot, and a staple cavity defined in the deck. The deck includes a proximal end and a distal end. The longitudinal slot extends from the proximal end toward the distal end. The staple is removably stored in the staple cavity. The staple driver is movably positioned in the staple cavity. The sled is movable from a proximal position to a distal position during a firing stroke. The sled is movable from the distal position toward the proximal position during a retraction stroke. The sled comprises a base, a central portion configured to move within the longitudinal slot, a first rail, a second rail, and a driver lift cam. The first rail is positioned on a first side of the central portion. The first rail comprises a first distal-facing ramp. The second rail is positioned on the first side of the central portion. The second rail comprises a second distal-facing ramp. The first distal-facing ramp and the second distal-facing ramp are configured to engage and move the staple driver from an unfired position to a fired position during the firing stroke. The driver lift cam is positioned intermediate the first rail and the second rail. The driver lift cam is configured to engage the staple driver and move the staple driver toward the fired position during the retraction stroke.

In accordance with the present disclosure, a surgical instrument comprising an end effector, a firing driver, and a staple cartridge seated in the end effector is disclosed. The firing driver is movable relative to the end effector from a proximal position to a distal position during a firing stroke and from the distal position to the proximal position during a retraction stroke. The staple cartridge comprises a cartridge body, a staple, a staple driver, and a sled. The cartridge body comprises a deck, a longitudinal slot, and a staple cavity defined in the deck. The deck includes a proximal end and a distal end. The longitudinal slot extends from the proximal end toward the distal end. The staple is removably stored in the staple cavity. The staple driver is movably positioned in the staple cavity. The sled is movable distally from an unfired position to a fired position by the firing driver during the firing stroke. The sled is movable proximally from the fired position to a returned position by the firing driver during the retraction stroke. The sled comprises a first sled component and a second sled component. The first sled component comprises a distal-facing ramp configured to engage and move the staple driver from an unfired position to a fired position during the firing stroke. The second sled component is movable relative to the first sled component. The second sled component comprises a proximal-facing ramp. The sled is configurable in a collapsed configuration and an expanded configuration. At least a portion of the proximal-facing ramp is nested within the first sled component when the sled is in the collapsed configuration. The sled is in the collapsed configuration during the firing stroke. The sled is in the expanded configuration during the retraction stroke. At least a portion of the proximal-facing ramp extends proximally relative to the first sled component when the sled is in the expanded configuration. The proximal-facing ramp is configured to engage and move the staple driver toward the fired position during the retraction stroke.

LISTING OF THE FIGURES

Various features of the embodiments described herein, together with advantages thereof, may be understood in accordance with the following description taken in conjunction with the accompanying drawings as follows:

FIG. 9 is a front perspective view of one of the staple drivers of the staple cartridge of FIG. 7;

FIG. 10 is back perspective view of the staple driver of FIG. 9;

FIG. 11 is a side elevational view of the staple driver of FIG. 9;

Corresponding reference characters indicate corresponding parts throughout the several views.

DETAILED DESCRIPTION

Figure 1:
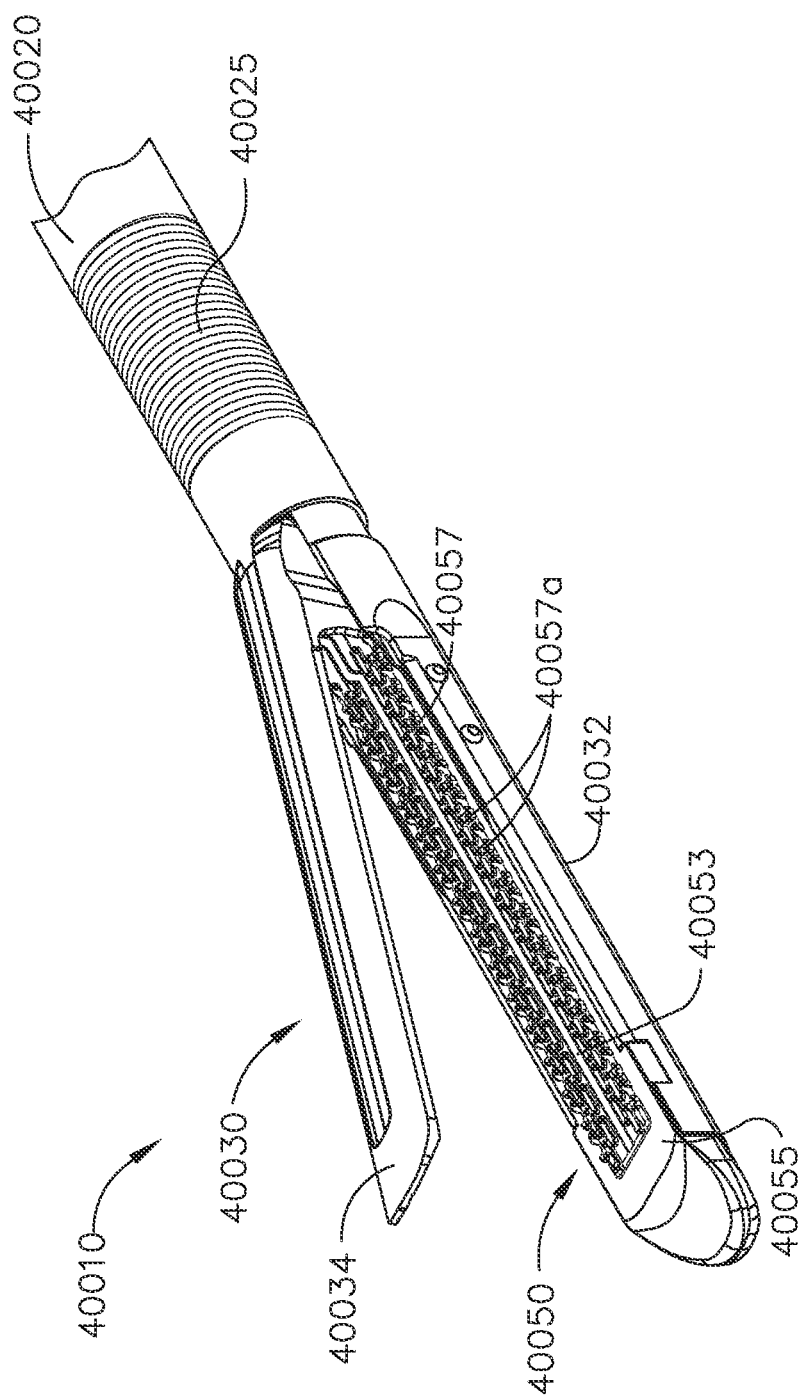
FIG. 1 is a partial perspective view of a stapling attachment for use with a surgical instrument depicting a staple cartridge positioned in an end effector of the stapling attachment, in accordance with the present disclosure.
Figure 2:
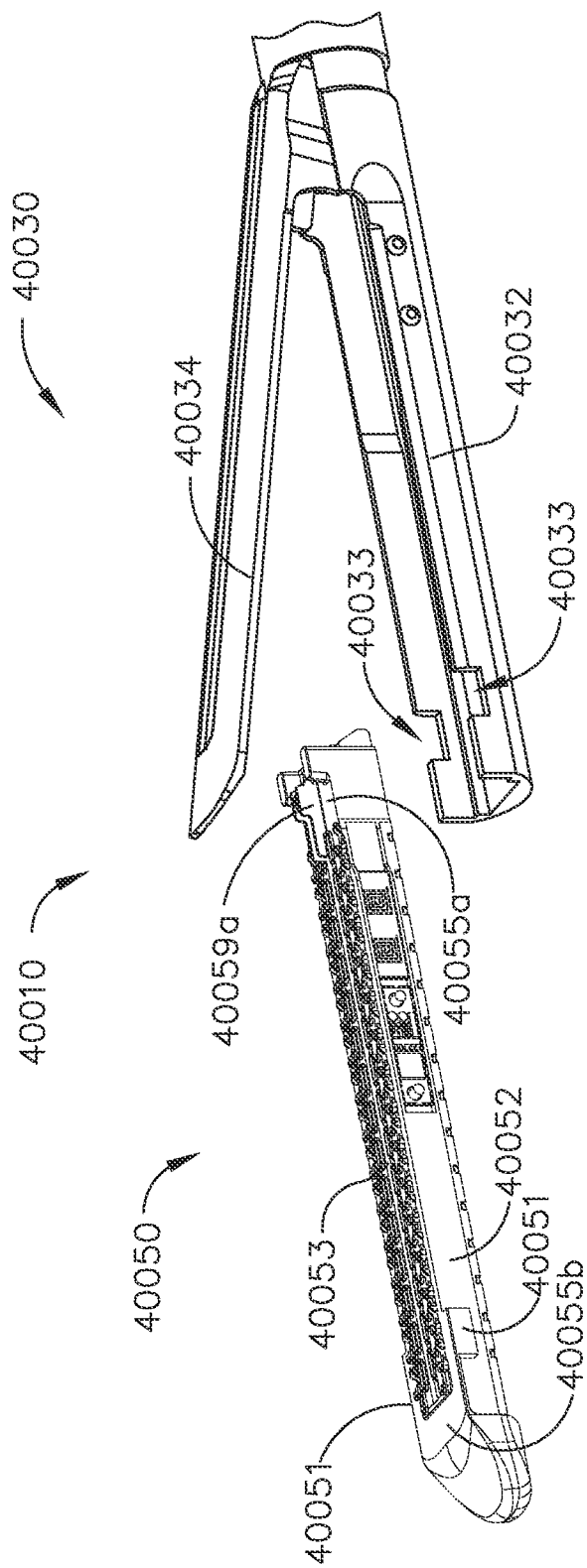
FIG. 2 is an exploded view of the stapling attachment of FIG. 1, depicting the staple cartridge separated from the end effector.

Applicant of the present application owns the following U.S. Patent Applications that were filed on even date herewith and which are each herein incorporated by reference in their respective entireties:

U.S. Patent Application, titled METHOD OF OPERATING A SURGICAL STAPLING INSTRUMENT; U.S. Pat. No. 18,379,759;

U.S. Patent Application, titled SURGICAL STAPLING SYSTEMS WITH ADAPTIVE STAPLE FIRING ALGORITHMS; U.S. Pat. No. 18,379,762;

U.S. Patent Application, titled LEARNED TRIGGERS FOR ADAPTIVE CONTROL OF SURGICAL STAPLING SYSTEMS; U.S. Pat. No. 18,379,763;

U.S. Patent Application, titled CONTROL CIRCUIT FOR ACTUATING MOTORIZED FUNCTION OF SURGICAL STAPLING INSTRUMENT UTILIZING INERTIAL DRIVE TRAIN PROPERTIES; U.S. Pat. No. 18,379,766;

U.S. Patent Application, titled PROPORTIONATE BALANCING OF THE FUNCTION IMPACT MAGNITUDE OF BATTERY OUTPUT TO PEAK MOTOR CURRENT; U.S. Pat. No. 18,379,768;

U.S. Patent Application, titled MOTOR OPTIMIZATION BY MINIMIZATION OF PARASITIC LOSSES AND TUNING MOTOR DRIVE CONFIGURATION; U.S. Pat. No. 18,379,771;

U.S. Patent Application, titled APPARATUS AND METHOD TO REDUCE PARASITIC LOSSES OF THE ELECTRICAL SYSTEM OF A SURGICAL INSTRUMENT; U.S. Pat. No. 18,379,773;

U.S. Patent Application, titled SURGICAL TOOL WITH RELAXED FLEX CIRCUIT ARTICULATION; U.S. Pat. No. 18,379,776;

U.S. Patent Application, titled WIRING HARNESS FOR SMART STAPLER WITH MULTI AXIS ARTICULATION; U.S. Pat. No. 18,379,777;

U.S. Patent Application, titled SURGICAL SYSTEM WITH WIRELESS ARRAY FOR POWER AND DATA TRANSFER; U.S. Pat. No. 18,379,781; and U.S. Patent Application, titled SURGICAL STAPLE CARTRIDGE COMPRISING REPLACEABLE ELECTRONICS PACKAGE; U.S. Pat. No. 18,379,784.

Applicant of the present application owns the following U.S. Patent Applications that were filed on even date herewith and which are each herein incorporated by reference in their respective entireties:

U.S. Patent Application, titled METHOD OF ASSEMBLING A STAPLE CARTRIDGE; U.S. Pat. No. 18,379,790;

U.S. Patent Application, titled CONTROL SURFACES ON A STAPLE DRIVER OF A SURGICAL STAPLE CARTRIDGE; U.S. Pat. No. 18,379,793;

U.S. Patent Application, titled INTEGRAL CARTRIDGE STIFFENING FEATURES TO REDUCE CARTRIDGE DEFLECTION; U.S. Pat. No. 18,379,796;

U.S. Patent Application, titled STAPLE CARTRIDGE COMPRISING WALL STRUCTURES TO REDUCE CARTRIDGE DEFLECTION; U.S. Pat. No. 18,379,801;

U.S. Patent Application, titled PAN-LESS STAPLE CARTRIDGE ASSEMBLY COMPRISING RETENTION FEATURES FOR HOLDING STAPLE DRIVERS AND SLED; U.S. Pat. No. 18,379,803;

U.S. Patent Application, titled SURGICAL STAPLE CARTRIDGES WITH SLEDS CONFIGURED TO BE COUPLED TO A FIRING DRIVER OF A COMPATIBLE SURGICAL STAPLER; U.S. Pat. No. 18,379,808;

U.S. Patent Application, titled STAPLE CARTRIDGE COMPRISING A COMPOSITE SLED; U.S. Pat. No. 18,379,810;

U.S. Patent Application, titled SURGICAL INSTRUMENTS WITH JAW AND FIRING ACTUATOR LOCKOUT ARRANGEMENTS LOCATED PROXIMAL TO A JAW PIVOT LOCATION; U.S. Pat. No. 18,379,811;

U.S. Patent Application, titled SURGICAL INSTRUMENTS WITH LATERALLY ENGAGEABLE LOCKING ARRANGEMENTS FOR LOCKING A FIRING ACTUATOR; U.S. Pat. No. 18,379,805;

U.S. Patent Application, titled DUAL INDEPENDENT KEYED LOCKING MEMBERS ACTING ON THE SAME DRIVE MEMBER; U.S. Pat. No. 18,379,817;

U.S. Patent Application, titled ADJUNCTS FOR USE WITH SURGICAL STAPLING INSTRUMENTS; U.S. Pat. No. 18,379,820;

U.S. Patent Application, titled ADJUNCTS FOR USE WITH SURGICAL STAPLING INSTRUMENTS; U.S. Pat. No. 18,379,822;

U.S. Patent Application, titled JAW CONTROL SURFACES ON A SURGICAL INSTRUMENT JAW; U.S. Pat. No. 18,379,826;

U.S. Patent Application, titled ZONED ALGORITHM ADAPTIVE CHANGES BASED ON CORRELATION OF COOPERATIVE COMPRESSION CONTRIBUTIONS OF TISSUE; U.S. Pat. No. 18,379,831;

U.S. Patent Application, titled STAPLE CARTRIDGES COMPRISING TRACE RETENTION FEATURES; U.S. Pat. No. 18,379,831; and U.S. Patent Application, titled STAPLE CARTRIDGES COMPRISING STAPLE RETENTION FEATURES; U.S. Pat. No. 18,379,832.

Numerous specific details are set forth to provide a thorough understanding of the overall structure, function, manufacture, and use of the embodiments as described in the specification and illustrated in the accompanying drawings. Well-known operations, components, and elements have not been described in detail so as not to obscure the embodiments described in the specification. The reader will understand that the embodiments described and illustrated herein are non-limiting examples, and thus it can be appreciated that the specific structural and functional details disclosed herein may be representative and illustrative. Variations and changes thereto may be made without departing from the scope of the claims.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Various exemplary devices and methods are provided for performing laparoscopic and minimally invasive surgical procedures. However, the reader will readily appreciate that the various methods and devices disclosed herein can be used in numerous surgical procedures and applications including, for example, in connection with open surgical procedures. As the present Detailed Description proceeds, the reader will further appreciate that the various instruments disclosed herein can be inserted into a body in any way, such as through a natural orifice, through an incision or puncture hole formed in tissue, etc. The working portions or end effector portions of the instruments can be inserted directly into a patient's body or can be inserted through an access device that has a working channel through which the end effector and elongate shaft of a surgical instrument can be advanced.

Figure 3:
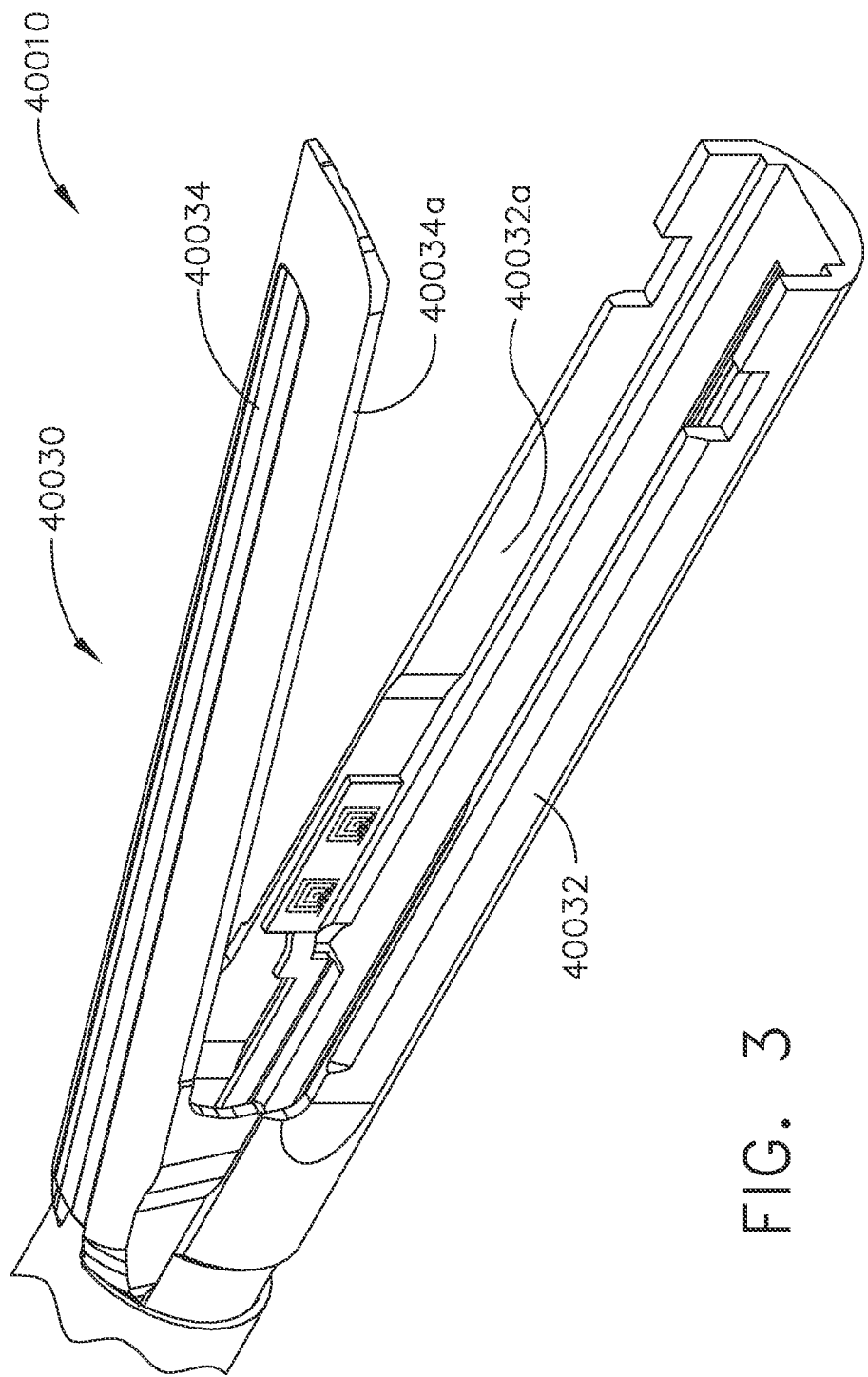
FIG. 3 is a partial perspective view of the stapling attachment of FIG. 1 depicting the end effector of the stapling attachment in an open configuration.
Figure 4:
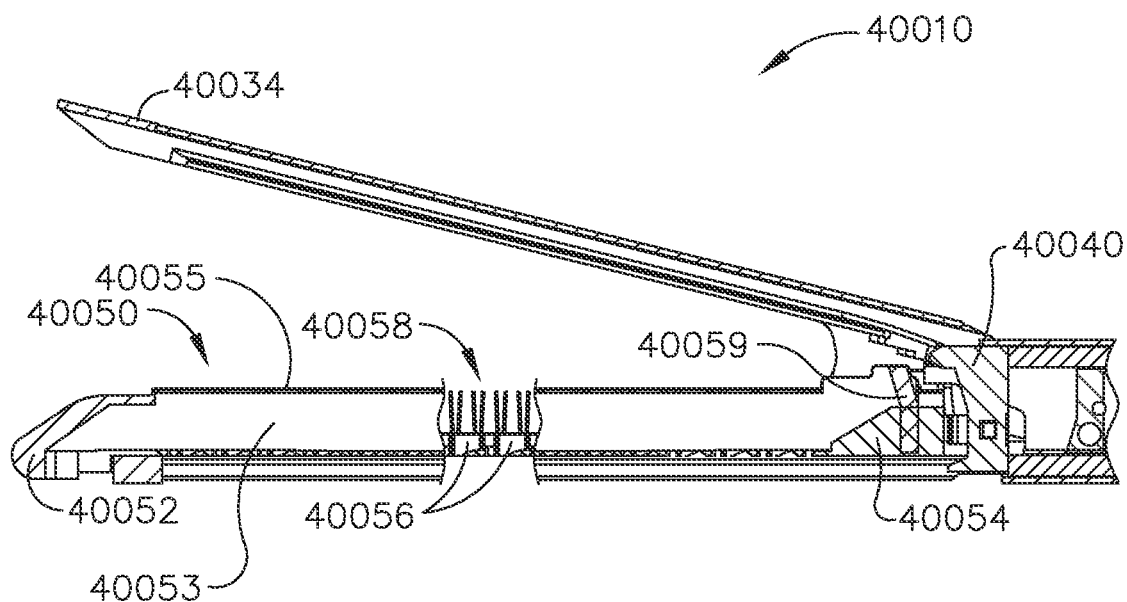
FIG. 4 is a partial cross-sectional view of the stapling attachment of FIG. 1 depicting the end effector in the open configuration.
Figure 5:
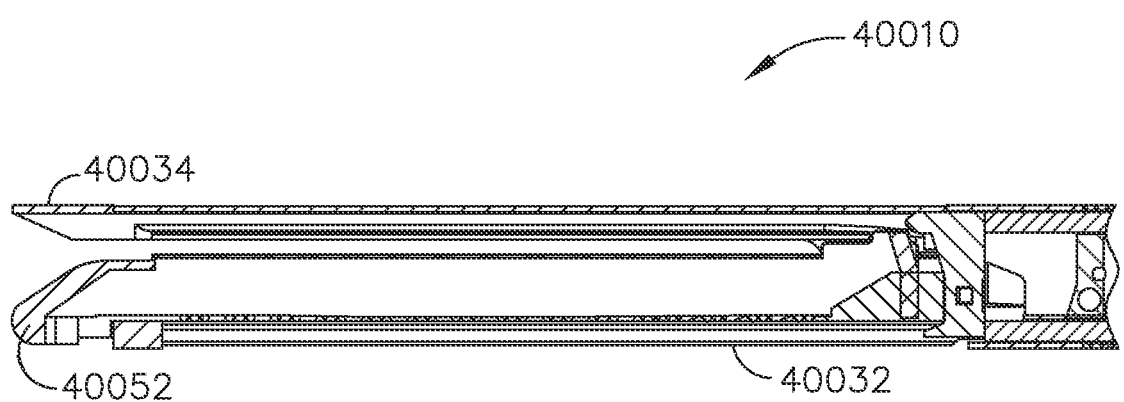
FIG. 5 is a partial cross-sectional view of the stapling attachment of FIG. 1 depicting the end effector in a closed configuration.

FIGS. 1-5 illustrate a stapling attachment 40010 for use with a surgical system. The stapling attachment 40010 comprises a shaft 40020 and an end effector 40030 extending from the shaft 40020. The stapling attachment 40010 further comprise an articulation joint 40025 positioned intermediate the end effector 40030 and the shaft 40020. The articulation joint 40025 is configured to permit the end effector 40030 to rotate relative to the shaft 40020 about the articulation joint 40025. The end effector 40030 comprises a first jaw 40032 and a second jaw 40034 movable relative to the first jaw 40032 between an open position (FIG. 4) and a closed position (FIG. 5) to capture the tissue of a patient therebetween. In accordance with the present disclosure, the second jaw 40034 may be movable relative to the first jaw 40032. Referring to FIG. 3, the first jaw 40032 comprises an elongate channel 40032*a* and the second jaw 40034 comprises an anvil 40034*a*. The elongate channel 40032*a* of the first jaw 40032 is configured to receive a replaceable staple cartridge 40050 therein that can be readily removed during a surgical procedure and replaced with a new staple cartridge; however, the first jaw 40032 may alternatively comprise a staple cartridge that is not replaceable. Referring primarily to FIG. 4, the staple cartridge 40050 comprises a cartridge body 40052, a sled 40054, a plurality of staple drivers 40056, and staples 40058 supported by the staple drivers 40056.

Further to the above, the cartridge body 40052 includes a longitudinal slot 40053 and a deck 40055 having a proximal end 40055*a* and a distal end 40055*b*. The longitudinal slot 40053 extends from the proximal end 40055*a* toward the distal end 40055*b*. The cartridge body 40052 further comprises a plurality of staple cavities 40057 defined in the cartridge body 40405. The staple cavities 40057 define a plurality of staple cavity openings 40057*a* defined in the deck 40055 of the cartridge body 40052. Referring primarily to FIG. 1, three rows of staple cavities 40057 are positioned on a first side of the longitudinal slot 40053 and three rows of staple cavities 40407 are positioned on a second side of the longitudinal slot 40053 opposite the first side. However, other arrangements of staple cavities and staples are contemplated. The staple cartridge 40050 further comprises lateral protrusions 40051 extending from the sides of the cartridge body 40052. The lateral protrusions 40051 are configured to be received in distal cutouts 40033 defined in the first jaw 40032 which can control the position of the staple cartridge 40050 in the first jaw 40032. The lateral protrusions 40051 and distal cutouts 40033, and/or other features of the staple cartridge 40050 and the first jaw 40032, may be configured to permit the staple cartridge 40050 to be snap-fit into the first jaw 40032.

Figure 6:
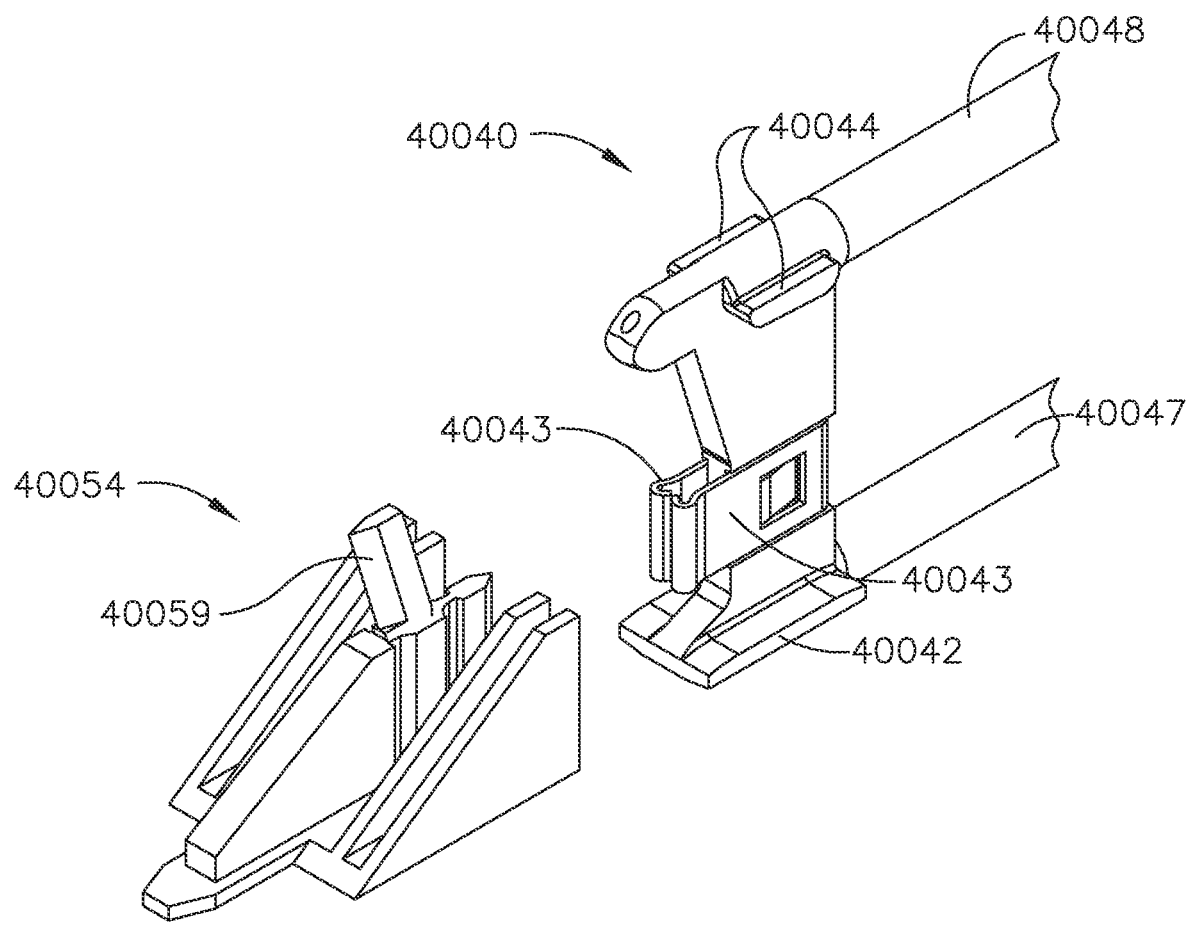
FIG. 6 is a partial perspective view of a firing driver of the stapling attachment of FIG. 1 and a sled of the staple cartridge of FIG. 1.

Referring now to FIGS. 4 and 6, the stapling attachment 40010 further comprises a firing driver 40040 movable relative to the end effector 40030 from a proximal position to a distal position during a firing stroke. The firing driver 40040 is configured to advance the sled 40054 relative to the staple cartridge 40050 from a proximal unfired position to a distal fired position during the firing stroke. The firing driver 40040 comprises a first cam 40042 configured to engage the first jaw 40032 during the firing stroke and second cams 40044 configured to engage the second jaw 40034 during the firing stroke. The firing driver 40040 further comprises a first firing bar, or rod, 40047 extending proximally from the firing driver 40040 and a second firing bar, or rod, 40048 extending proximally from the firing driver 40040. The first firing bar 40047 is spaced apart from the second firing bar 40048. The first and second firing bars 40047, 40048 are configured to transfer a firing motion from the surgical system to the firing driver 40040 to translate the firing driver 40040 distally during the staple firing stroke and then proximally during a retraction stroke. The surgical system can comprise an electric motor and a motor control circuit which moves the firing driver 40040 that is responsive to an input from a clinician and/or a robotic surgical system.

Further to the above, referring primarily to FIG. 6, the sled 40054 of the staple cartridge 40050 comprises a knife 40059. However, the firing driver 40040 may comprise the knife instead of the sled 40054. In any event, when the sled 40054 is in the proximal unfired position, as illustrated in FIG. 4, the knife 40059 is positioned within a proximal knife housing 40059a of the cartridge body 40052. As such, during shipping and assembly of the staple cartridge 40050, the knife 40059 of the sled 40054 is positioned within the knife housing 40059a and, thus, the chances of a user coming into contact with the knife 40059 when handling the staple cartridge 40050 is reduced (see FIG. 2).

In use, referring to FIG. 6, the firing driver 40040 is positioned proximal to—and not in contact with—the sled 40054 when the staple cartridge 40050 is seated in the first jaw 40032. The firing driver 40040 is advanced toward the sled 40054 at the outset of the firing stroke and engages the sled 40054 to advance the sled 40054 through the remainder of the firing stroke. More specifically, the firing driver 40040 comprises a pair of opposing lateral spring arms 40043 extending distally therefrom that engage, grip, and push the sled 40054 distally during the firing stroke. Moreover, the lateral spring arms 40043 couple the firing driver 40040 to the sled 40054 such that the sled 40054 is retractable by the firing driver 40040 during a retraction stroke. In accordance with the present disclosure, the firing driver 40040 can be configured to retract the sled 40054 proximally all the way into its original proximal unfired position. The staple cartridge 40050 further comprises a stop that is engaged by the sled 40054 when the sled 40054 is pulled back into its proximal unfired position by the firing driver 40040 such that, as the firing driver 40040 is retracted further back into its original proximal unfired position, the firing driver 40040 disengages from the sled 40054. Alternatively, the firing driver 40040 and sled 40054 may be one unitary structure which is movable relative to the end effector 40030. In such instances, the sled 40054 is part of the stapling attachment 40010 and not part of the staple cartridge 40050.

Figure 7:
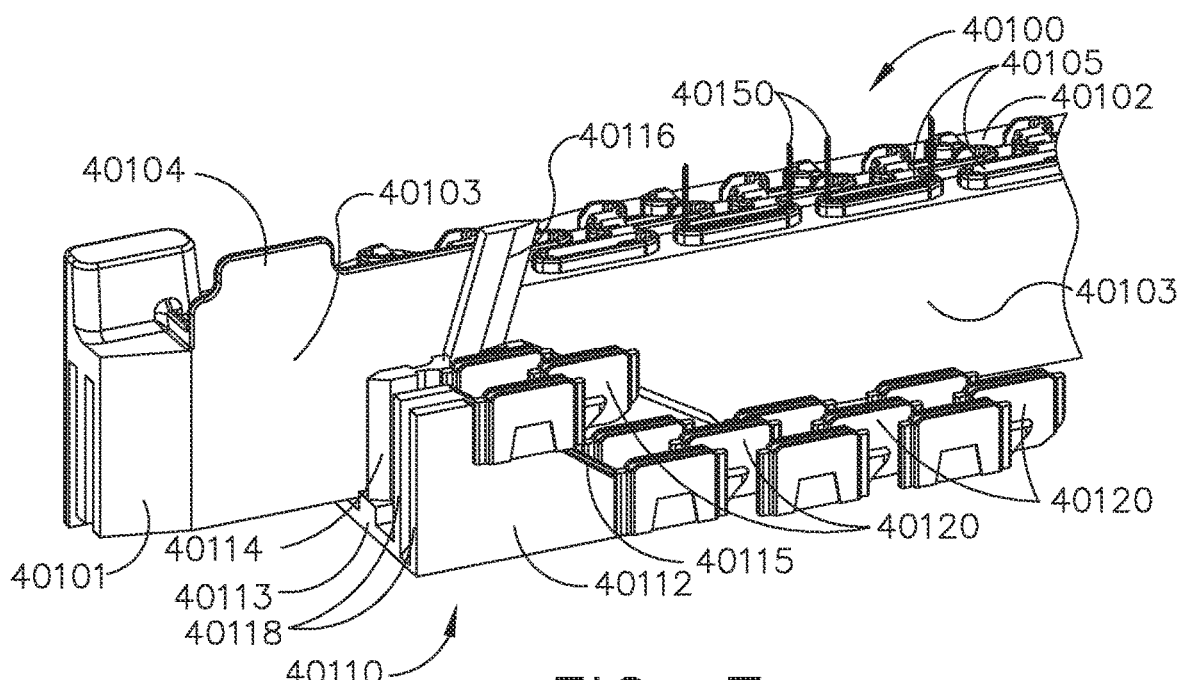
FIG. 7 is a partial perspective view of a staple cartridge depicting staple drivers and a sled in a partially fired position in accordance with the present disclosure.

FIGS. 7-11 depict a staple cartridge 40100 for use with a surgical instrument. The staple cartridge 40100 comprises a cartridge body 40101, a sled 40110, a plurality of staple drivers 40120 arranged in longitudinal rows, and staples 40150 supported by the staple drivers 40120. The cartridge body 40101 includes a longitudinal slot 40103, a deck 40102, and a plurality of staple cavities 40105 define in the deck 40102. The cartridge body 40101 further comprises a proximal knife housing 40104 at the proximal end of the longitudinal slot 40103. Referring primarily to FIG. 7, three rows of staple cavities 40105 may be positioned on a first side of the longitudinal slot 40103 and three rows of staple cavities 40105 are positioned on a second side of the longitudinal slot 40103 opposite the first side. In use, the staple cartridge 40100 is positioned on a first side of patient tissue that is to be stapled and an anvil, such as the anvil 40034, for example, is positioned on a second side of the patient tissue. The anvil 40034 is moved toward the staple cartridge 40100 to compress and clamp the tissue against the deck 40055; however, the staple cartridge 40100 may alternatively be moved toward the anvil 40034 to compress and clamp tissue against the deck 40055. After the patient tissue has been clamped, or captured between, the jaws, the staple firing stroke can be performed, as discussed further below.

During the staple firing stroke, the sled 40110 is pushed distally by the firing driver 40040 to engage the staple drivers 40120 and eject the staples 40150 supported on the staple drivers 40120 into the captured patient tissue. The staple drivers 40120 are movably positioned in the staple cavities 40105 and are movable between a first, or unfired, position and a second, or fired, position by the sled 40110 to eject the staples 40150 from the staple cavities 40105. FIG. 9 illustrates that the staple drivers 40120 are triple staple drivers configured to simultaneously eject three staples; however, other staple drivers are contemplated which are configured to eject one, two, or more than three staples. The drivers 40120 may be retained in the cartridge body 40101 by a retainer, or pan, which extends at least partially around the bottom of the cartridge body 40101 and includes resilient members configured to grip the cartridge body 40101 and hold the retainer to the cartridge body 40101. The drivers 40120 are movable between their unfired positions and their fired positions by the sled 40110 to eject the staples from the cartridge body 40101, as discussed in greater detail below.

Returning to FIG. 7, the sled 40110 comprises a base 40113, a plurality of rails 40112 extending upwardly from the base 40113, and a central portion 40114 extending upwardly from the base 40113. The central portion 40114 comprises a knife 40116 extending therefrom. Further, each of the rails 40112 comprises a distal ramp portion 40115 thereon. The sled 40110 is movable distally from a proximal unfired position to a distal fired position during a staple firing stroke and movable proximally from the distal fired position to the proximal unfired position during a retraction stroke by a firing member of the surgical instrument, such as the firing driver 40040 (see FIG. 6). The central portion 40114 and the knife 40116 of the sled 40110 are configured to move within the longitudinal slot 40103 of the cartridge body 40101 during the staple firing stroke and the retraction stroke. At least a portion of the knife 40116 is stored in the proximal knife housing 40104 of the cartridge body 40101 when the sled 40110 is in the proximal unfired position. The knife 40116 comprises a distally-presented cutting edge that is exposed when the sled 40110 is moved distally at the beginning of the staple firing stroke. Further, as discussed in greater detail below, the distal ramps 40115 of the sled 40110 engage each of the staple drivers 40120 and move the staple drivers 40120 from their unfired positions to their fired positions during the staple firing stroke.

Referring primarily to FIGS. 9-11, each staple driver 40120 comprises a plurality of staple supports comprising an inner staple support 40122, a central staple support 40124, and an outer staple support 40126. The inner staple support 40122 is positioned closest to the longitudinal slot 40103 of the cartridge body 40101 and the outer staple support 40126 is positioned farthest away from the longitudinal slot 40103 of the cartridge body 40101. Each of the staple supports 40122, 40124, 40126 are configured to support a staple 40150 thereon. The inner staple support 40122 is connected to the central staple support 40124 by an inner lateral bridge 40128*a* and the outer staple support 40126 is connected to the central staple support 40124 by an outer lateral bridge 40128*b*. The inner lateral bridge 40128*a* comprises an inner proximal camming surface 40129*a* and the outer lateral bridge 40128*b* comprises an outer proximal camming surface 40129*b* which are positioned on opposite sides of the central staple support 40124. In use, the distal ramps 40115 of the sled 40110 on one side of the longitudinal slot 40103 are configured to engage the inner proximal camming surface 40129*a* and the outer proximal camming surface 40129*b* of each driver 40120 to eject the staples 40150 positioned on the staple supports 40122, 40124, 40126 from the cartridge body 40101 during the staple firing stroke. Similarly, the distal ramps 40115 on the other side of the sled 40110 engage the drivers 40120 on the other side of the longitudinal slot 40103 to eject the staples positioned thereon.

Figure 8:
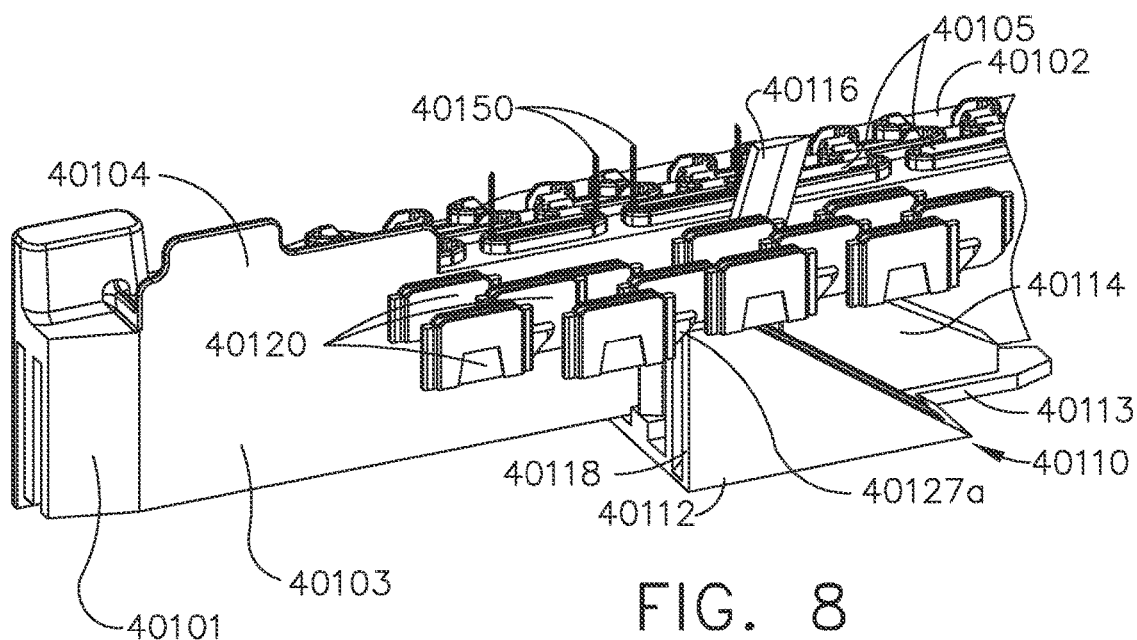
FIG. 8 is a partial perspective view of the staple cartridge of FIG. 7 with the sled in a partially retracted position.

Further to the above, once all of the staple drivers 40120 have been moved from their unfired positions to their fired positions, the sled 40110 is retracted from its distal fired position toward a proximal position. In accordance with the present disclosure, the staple drivers 40120 can be sized and configured such that they fit closely within their respective staple cavities such that, once such staple drivers 40120 are moved to their fired positions, they remain in their fired positions. The perimeters of the staple supports 40122, 40124, 40126 can have a line-to-line fit with the perimeters of the staple cavities In such instances, the sled 40110 may easily pass under the staple drivers 40120 as the sled 40110 is retracted proximally by the firing driver 40040. However, one or more of the staple drivers 40120 may fall into or toward their unfired position and into the path of the sled 40110 as the sled 40110 is being retracted. FIG. 8 illustrates the sled 40110 during a retraction stroke where one of the triple staple drivers 40120 has fallen slightly from its fired position and into the path of the rails 40112 of the sled 40110. Specifically, the inner and outer lateral bridges 40128*a*, 40128*b* of the staple driver 40120 are aligned with the rails 40112 of the sled 40110, as discussed above, and therefore the inner and outer lateral bridges 40128*a*, 40128*b* are positioned in the return path of the rails 40112 of the sled 40112 in FIG. 8.

Further to the above, referring to FIG. 9, the inner and outer lateral bridges 40128*a*, 40128*b* of the staple drivers 40120 further comprise inner and outer distal camming surfaces 40127*a*, 40127*b* thereon. As such, when the sled 40110 is retracted, proximal vertical faces 40118 of the sled rails 40112 engage the inner and outer distal camming surfaces 40127*a*, 40127*b* of the fallen driver 40120 to move the fallen driver 40120 toward its fired position to permit the sled 40110 to pass thereunder and be retracted. In other words, once the fallen driver 40120 is moved back into its fired position, the sled 40110 is able to pass underneath the fallen driver 40120 and move to its proximal or fully retracted position. One or more staple drivers 40120 may move completely into their unfired positions such that, when the sled 40110 is retracted, the interaction between the proximal vertical faces 40118 of the sled rails 40112 and the inner and outer distal camming surfaces 40127*a*, 40127*b* of the fallen driver 40120 may not be enough to lift the staple driver 40120 from its unfired position. As such, it may be advantageous to include a proximally facing ramp on the sled rails 40112 to aid in lifting the driver 40120 from its unfired position toward its fired position, as discussed in greater detail below.

Figure 12:
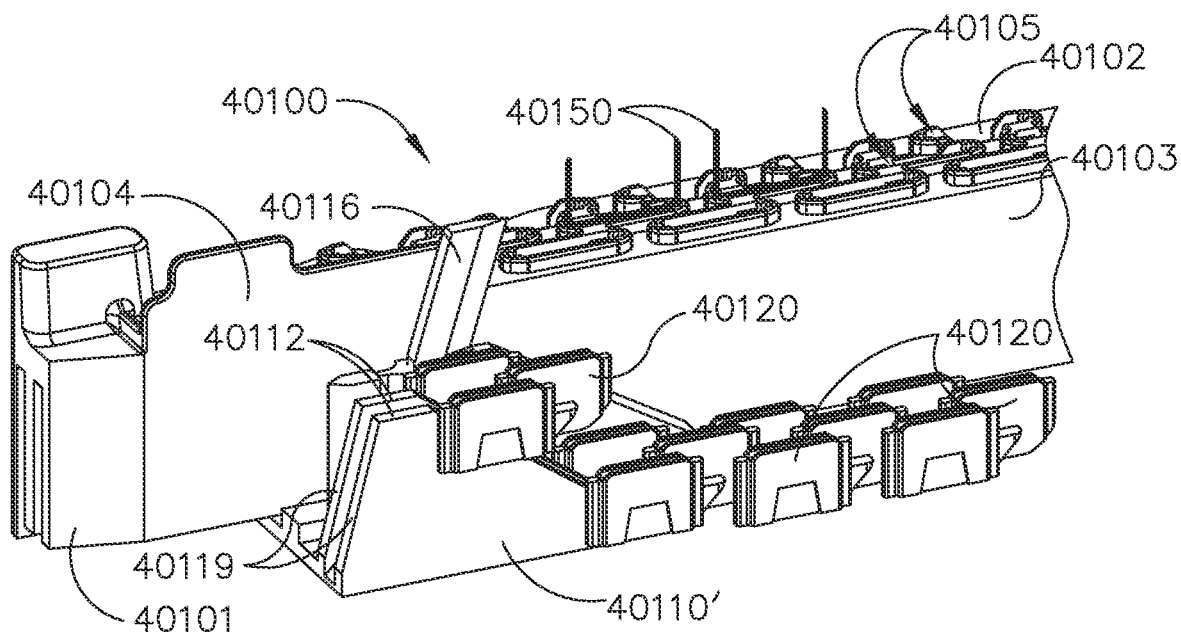
FIG. 12 is a partial perspective view of a staple cartridge depicting a sled of the staple cartridge in a partially fired position in accordance with the present disclosure.
Figure 13:
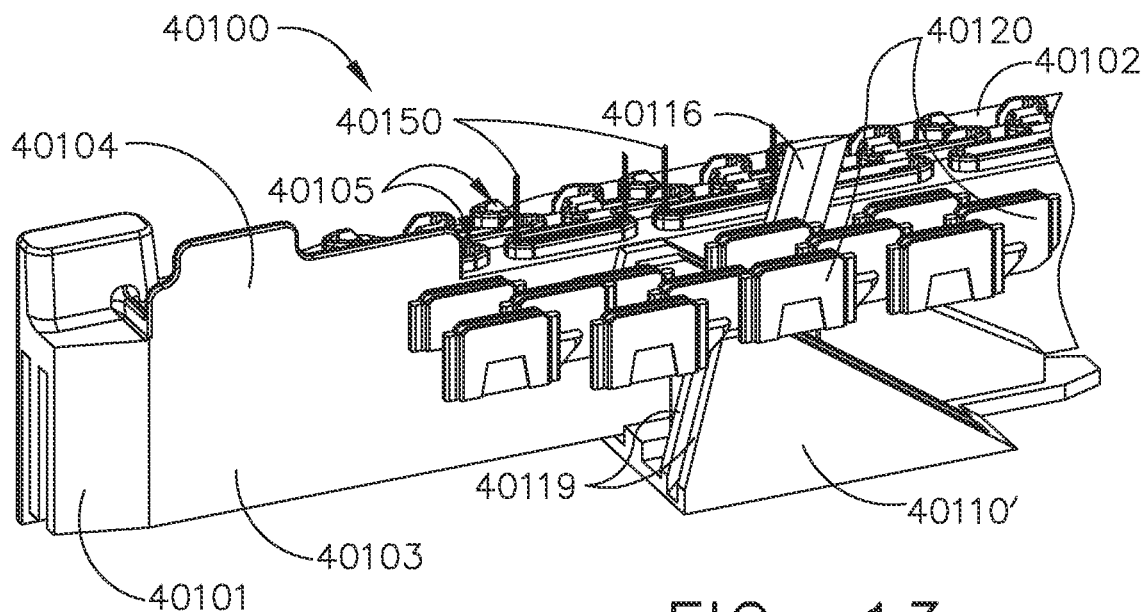
FIG. 13 is a partial perspective view of the staple cartridge of FIG. 12 with the sled in a partially retracted position.

FIGS. 12 and 13 illustrate a sled 40110' for use with the staple cartridge 40100. The sled 40110' comprises rails 40112 which each includes a proximal ramp 40119 facing proximally. The proximal ramps 40119 are configured to engage the inner and outer distal camming surfaces 40127*a*, 40127*b* of a dropped or fallen staple driver 40120 when the sled 40110' is retracted. Notably, the proximal ramps 40119 extend from the top of the rails 40112 all the way down to the bottom of the sled 40110'. As such, the proximal ramps 40119 are configured to engage a staple driver 40120 in any position-partially fallen or completely fallen—and lift the staple driver 40120 upwardly during the retraction stroke to make clearance for the sled 40110'. In accordance with the present disclosure, however, the angle on the ramps 40119 can be steep. Steep angles on the ramps 40119 may be common when there are space constraints within the surgical instrument. As such, a sled can comprise features that first lift a fallen staple driver from its unfired position to an intermediate position using a first portion of the sled and then lift the fallen staple driver from the intermediate position into its fired position using a second portion of the sled, as discussed in greater detail below.

FIGS. 14-17 illustrate a staple cartridge 40300 for use with a surgical stapling instrument, such as those described herein. The staple cartridge 40300 is similar to the staple cartridges 40100 in many respects. For instance, the staple cartridge 40300 may comprise the cartridge body 40101, the deck 40102, the longitudinal slot 40103, the staple cavities 40105, the staple drivers 40120, and the staples 40150, discussed above. Further, the staple cartridge 40300 comprises a sled 40310 that is movable distally during a staple firing stroke to drive the staple drivers 40120 upwardly and eject the staples 40150 stored in the staple cartridge 40300. The sled 40310 comprises a base 40313, a plurality of rails 40312 extending upwardly from the base 40313, and a central portion 40314 also extending upwardly from the base 40313 (see FIG. 17). The central portion 40314 comprises a knife 40316 extending therefrom and is configured to translate within a longitudinal slot defined in the staple cartridge 40300. Each of the rails 40312 comprises a distal ramp portion 40315 facing distally that is configured to engage the staple drivers 40120.

Further to the above, the region of the base 40313 of the sled 40310 in between the rails 40312 at the distal end 40319*b* of the base 40313 is configured to provide an initial lift to one or more of the staple drivers 40120 during the firing stroke of the sled 40310. Specifically, the distal end 40319*b* of the base 40313 in between the rails 40312 is configured to contact the central staple support 40124 of the staple driver 40120 prior to the distal ramps 40315 of the sled 40310 engaging an inner proximal camming surface 40129*a* and an outer proximal camming surface 40129*b* of the staple driver 40120. As such, the base 40313 of the sled 40310 is configured to initially lift the staple driver 40120 from its unfired position to an intermediate position and then the distal ramps 40315 of the sled 40310 are configured to engage the staple driver 40120 to move the staple driver 40120 from the intermediate position to the fired position.

In use, further to the above, the sled 40310 is movable distally from a proximal position to a distal position during a staple firing stroke and movable proximally from the distal position to the proximal position during a retraction stroke by a firing driver of a surgical instrument, such as the firing driver 40040 (see FIG. 6). During the staple firing stroke, as described above, the distal ramps 40315 of the sled 40310 are configured to engage the staple drivers 40120 to move the staple drivers 40120 from their unfired positions to their fired positions. Once the firing stroke is complete, further to the above, one or more of the staple drivers 40120 may fall from their fired positions toward and/or into their unfired positions and, thus, into the path of the rails 40312 of the sled 40310. As discussed in greater detail below, the sled 40310 is configured to move the fallen staple drivers 40120 into their fired positions during the retraction stroke to permit the sled 40310 to be retracted.

Figure 17:
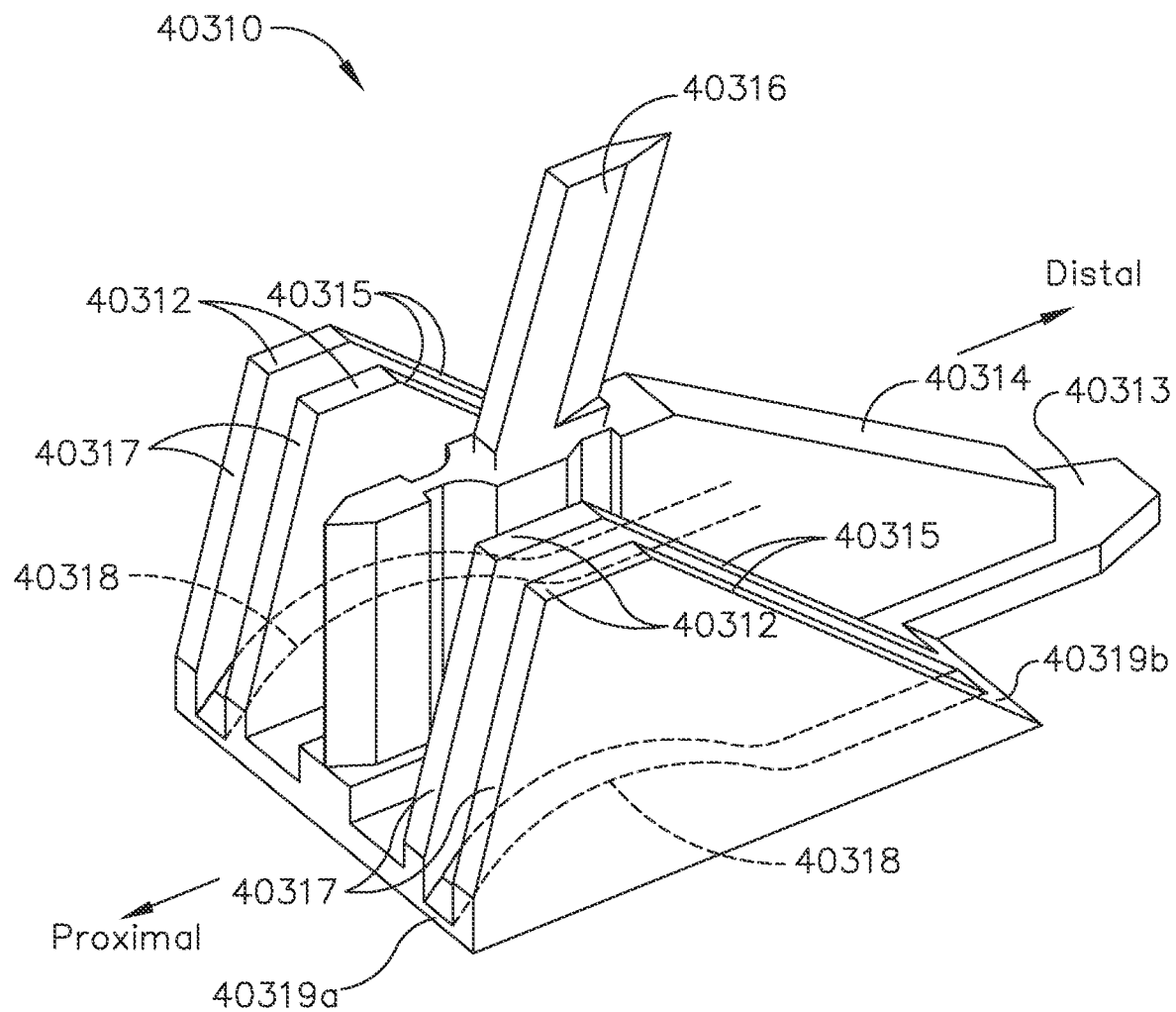
FIG. 17 is a perspective view of the sled of the staple cartridge of FIG. 14.
Figure 18:
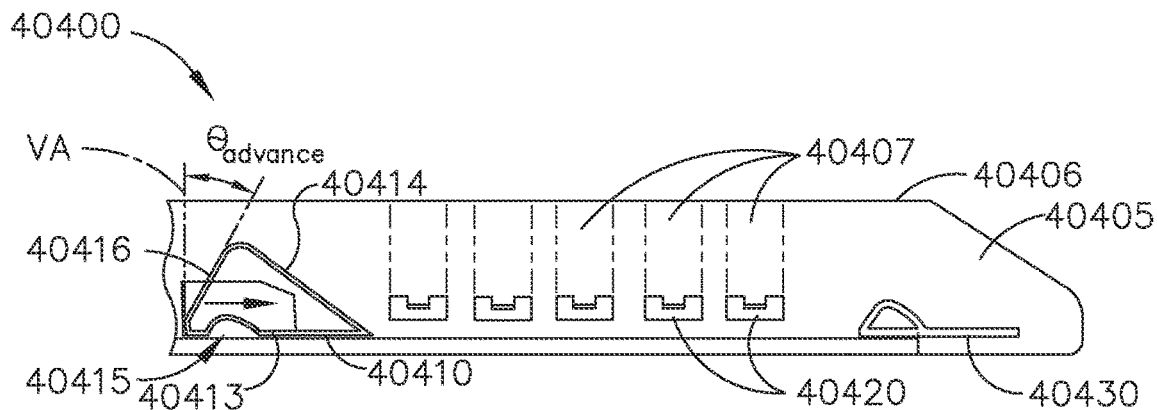
FIG. 18 is a partial cross-sectional view of a staple cartridge for use with a surgical instrument depicting a sled assembly of the staple cartridge in a proximal unfired position in accordance with the present disclosure.

Further to the above, referring again to FIG. 17, each lateral side of the sled 40310 comprises two rails 40312. In addition to a distal ramp 40315, each rail 40312 further comprises a proximal ramp portion 40317 facing proximally. The base 40313 comprises a proximal end 40319a and a distal end 40319b, with the distal end 40319b located in the region of the rails 40312. The base 40313 further comprises a driver lift cam 40318 positioned intermediate the rails 40312 on each side of the central portion 40314 of the sled 40310. Referring primarily to FIG. 17, each driver lift cam 40318 comprises an arcuate protrusion extending upwardly from the base 40313. The driver lift cam 40318 tapers downwardly toward the proximal end 40319a of the base 40313 such that the thickness of the base 40313 at the proximal end 40319a is reduced or recessed, i.e., less than the general thickness of the base 40313. The drive lift cams 40318 and the proximally facing ramps 40317 of the sled 40310 are configured to engage and lift one or more fallen staple drivers 40120 toward their fired positions during a retraction stroke of the sled 40310, as discussed in greater detail below.

Figure 14:
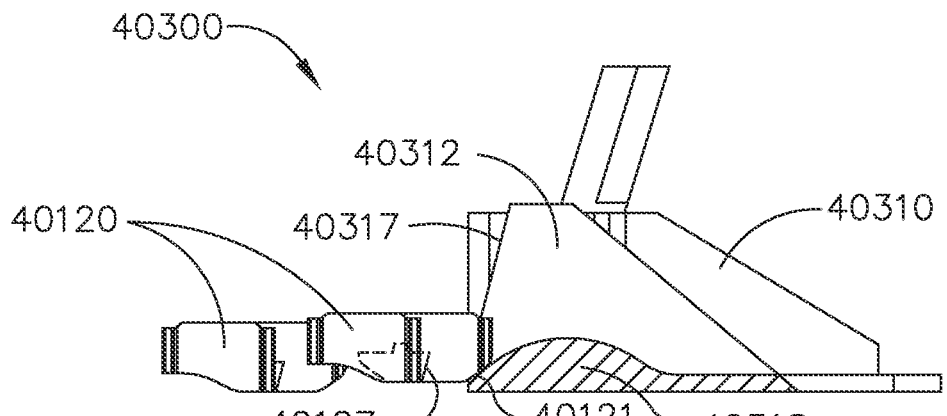
FIG. 14 is a partial cross-sectional side view of a staple cartridge illustrated with components removed depicting a sled of the staple cartridge in a first retracted position in accordance with the present disclosure.
Figure 15:
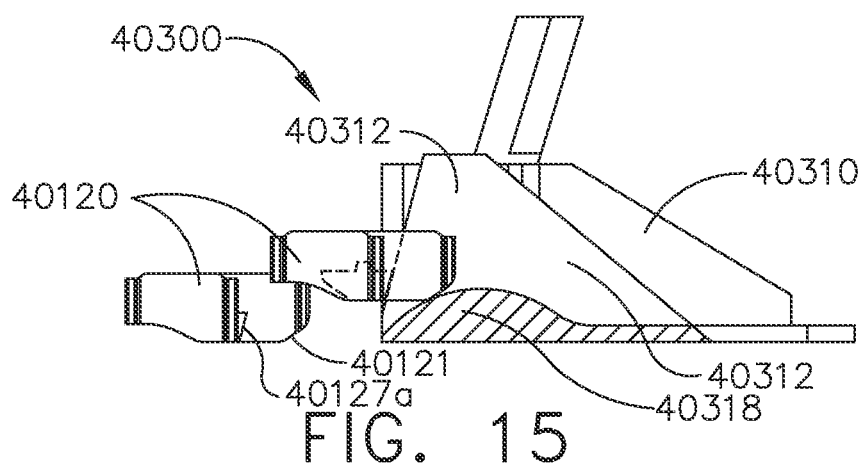
FIG. 15 is a partial cross-sectional side view of the staple cartridge of FIG. 14 illustrated with components removed with the sled in a second retracted position.

FIG. 14 illustrates two of the drivers 40120 which have fallen from their fired positions with the sled 40310 positioned distal to the drivers 40120 after the firing stroke has been completed, or at least partially completed. As the sled 40310 is retracted proximally from its position in FIG. 14, a driver lift cam 40318 of the sled 40310 engages a distal ramp 40121 (see FIGS. 9 and 11) of the central staple support 40124 of the staple driver 40120 to initially move the staple driver 40120 from a fallen position toward its fired position as shown in FIG. 14. Further proximal retraction of the sled 40130 results in the driver lift cam 40318 continuing to engage the distal ramp 40121 to move the staple driver 40120 into an intermediate position illustrated in FIG. 15. The driver lift cam 40318 can be configured to move the staple driver 40120 a minimum distance toward its fired position. The minimum distance may be between 0.033 to 0.045 inches (i.e., 0.083 to 0.114 cm), for example, or at least half of the overall height of the driver 40120.

Figure 16:
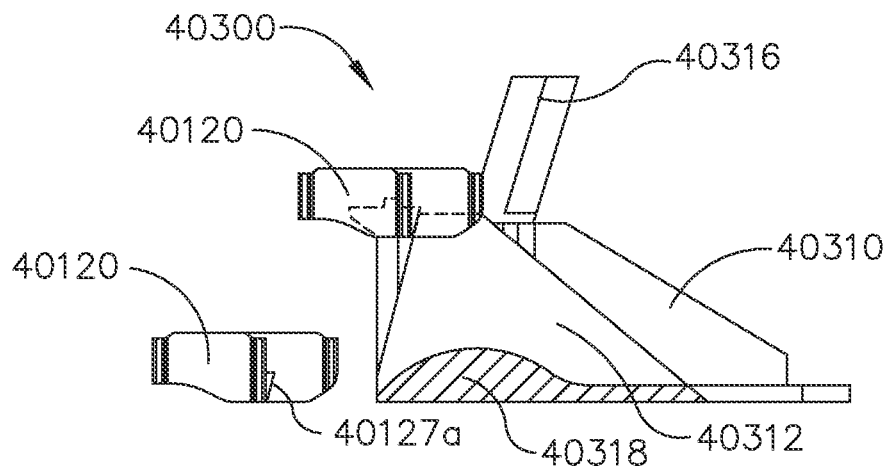
FIG. 16 is a partial cross-sectional side view of the staple cartridge of FIG. 14 illustrated with components removed with the sled in a third retracted position.

Further to the above, when the staple driver 40120 is in the intermediate position, the proximal ramps 40317 of the sled 40130 abut the inner and outer distal camming surfaces 40127a, 40127b (see FIG. 9) of the staple driver 40120. As the sled 40130 is retracted further proximally from its position in FIG. 15 to its position in FIG. 16, the proximal ramps 40317 continue to engage the inner and outer distal camming surfaces 40127a, 40127b of the staple driver 40120 and move the staple driver 40120 from its intermediate position in FIG. 15 into its fired position (FIG. 16). Once the fallen staple drivers 40120 is moved into its fired position, the sled 40310 is permitted to pass by the staple drivers 40120. This same process is repeated for any of the staple drivers 40120 that may have moved from their fired positions into the retraction path of the sled 40130 as the sled 40130 is retracted to its proximal position.

Further to the above, the angle of the inner and outer distal camming surfaces 40127a, 40127b compliment the angle of the proximal ramps 40317. In accordance with the present disclosure, the proximal ramps 40317 of the rails 40312 may comprise a slope that matches the slope of the camming surfaces 40127a, 40127b. The proximal ramps 40317 of the rails 40312 may comprise a more gradual slope than the proximal ramps 40317 depicted in FIGS. 14-17. The angles of the inner and outer distal camming surfaces 40127a, 40127b of the staple driver 40120 may correspond to the gradual slope of the proximal ramps 40317. It may be advantageous to have as gradual of a proximal sloped ramp on the sled as possible without unnecessarily lengthening the sled 40310 in order to provide better mechanical leverage when lifting a fallen staple driver. As discussed in greater detail below, it may be advantageous for the distal ramps 40315 to have a first angle and the proximal ramps 40317 to have a second angle that is different from the first angle.

FIGS. 18-22 illustrate a staple cartridge 40400 for use with a surgical stapling instrument such as those disclosed herein. The staple cartridge 40400 comprises a cartridge body 40405, a sled 40410, a plurality of staple drivers 40420 arranged in longitudinal rows, staples (not shown in FIGS. 18-22) supported by the staple drivers 40420, and a sled lift cam 40430. The cartridge body 40405 includes a longitudinal slot defining a longitudinal axis, a proximal end, a distal end, and a deck 40406 extending intermediate the proximal end and the distal end. The cartridge body 40405 further comprises a plurality of staple cavities 40407 defined in the cartridge body 40405. The staple cavities 40407 define a plurality of staple cavity openings in the deck 40406 of the cartridge body 40405. Three rows of staple cavities 40407 are positioned on a first side of the longitudinal slot and three rows of staple cavities 40407 can be positioned on a second side of the longitudinal slot. Other arrangements of staple cavities and staples are contemplated. In use, the staple cartridge 40400 is positioned on a first side of the tissue to be stapled and the anvil is positioned on a second side of the tissue to be stapled. The anvil is moved toward the staple cartridge to compress and clamp the tissue against the deck 40406; however, the staple cartridge 40400 may be moved toward the anvil to compress and clamp tissue against the deck 40406. Thereafter, staples removably stored in the cartridge body 40405 can be deployed into the tissue.

Further to the above, the staple drivers 40420 may be similar or identical to the staple drivers 40120 discussed herein. However, other staple driver arrangements are contemplated. The staple drivers 40420 are movably positioned in the staple cavities 40407 such that their movement is constrained to vertical movement by the walls of the staple cavities 40407.

Figure 22:
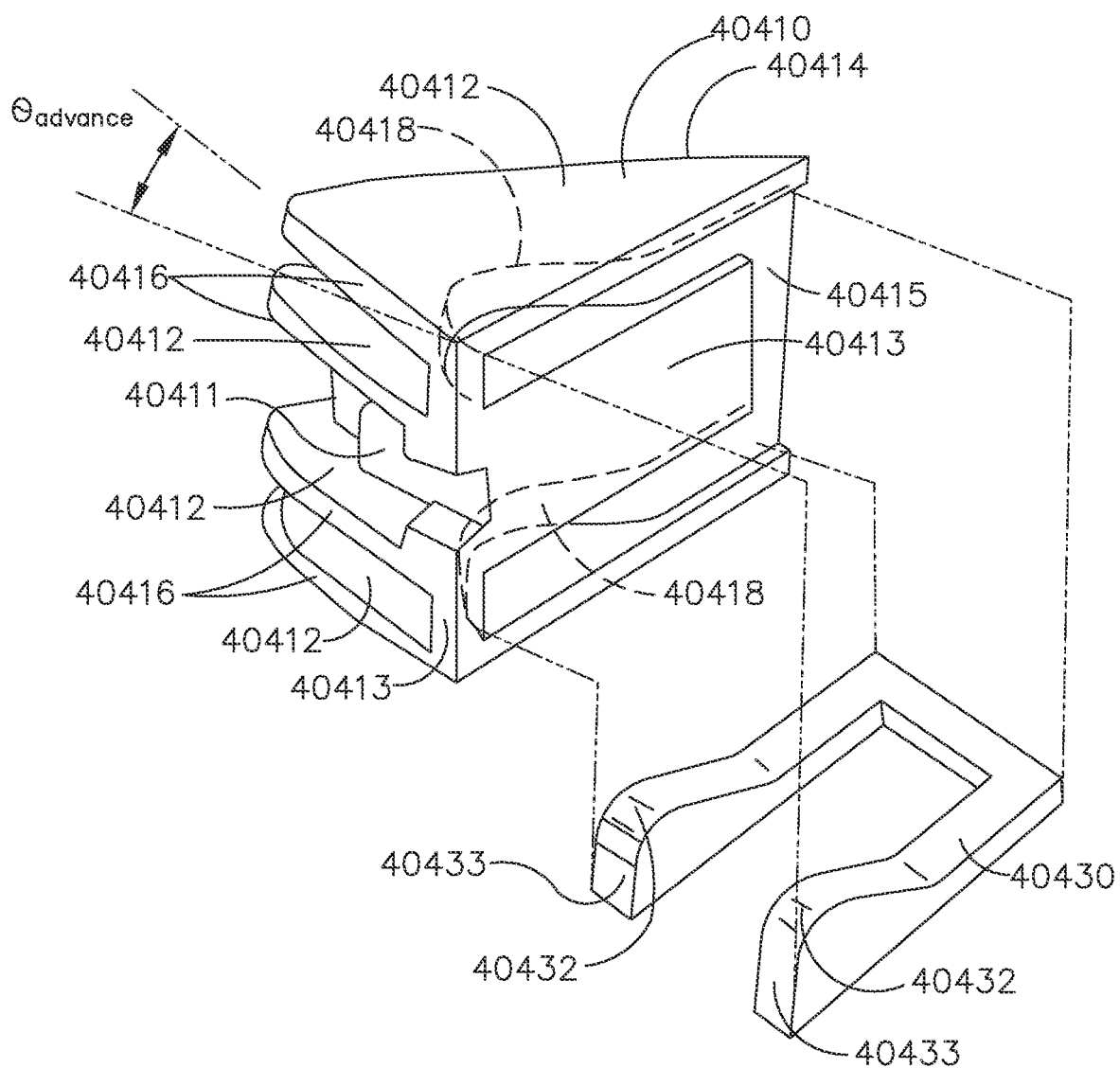
FIG. 22 is an exploded view of the sled assembly of the staple cartridge of FIG. 18 depicting a distal driver lift cam.

Referring primarily to FIG. 22, the sled 40410 comprises a base 40413, a central portion 40411, and a plurality of rails 40412 extending from the base 40413. As discussed herein, the central portion 40411 is configured to travel within a longitudinal slot of the staple cartridge body 40405. The central portion 40411 may comprise a knife, such as the knife 40316 (FIG. 17), for example. Further, FIG. 22 illustrates that there are two rails 40412 on each side of the central portion 40411. Each of the rails 40412 comprises a distal ramp 40414 facing distally and a proximal ramp 40416 facing proximally. The base 40413 of the sled 40410 further comprises a driver lift cam 40418 at its proximal end intermediate the rails 40412 on both sides of the central portion 40411. The sled 40410 further comprises a bottom cutout region 40415 defined in the base 40413 of the sled 40410. The cutout region 40415 extends proximally in between the rails 40412 on each side of the central portion 40411 of the sled 40410 and at least partially into the driver lift cam 40418. The driver lift cam 40418 may be similar to or identical to the driver lift cam 40318 (FIG. 17) and operate in a similar or identical manner, for example. The cutout region 40415 is defined in the base 40413 and the driver lift cam 40418 to provide room for the sled lift cam 40430, as discussed in greater detail below.

Figure 19:
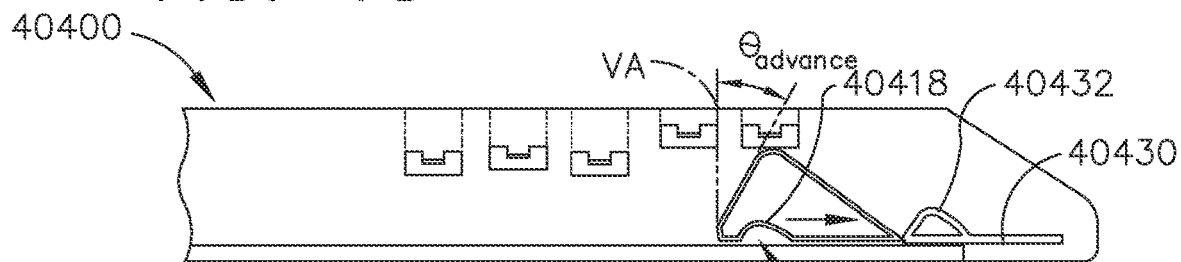
FIG. 19 is a partial cross-sectional view of the staple cartridge of FIG. 18 depicting the sled assembly in an intermediate position distal to the proximal unfired position.

Further to the above, the sled 40410 is movable from a proximal unfired position (FIG. 18) to a distal fired position (FIG. 20) during a firing stroke by a firing driver of the surgical instrument such as those discussed herein. Also further to the above, the sled 40410 is movable from the distal fired position (FIG. 20) to the proximal unfired position (FIG. 18) during a retraction stroke by the firing driver after at least a portion of the firing stroke is completed. In use, the distal ramps 40414 of the sled 40410 are configured to engage and move the staple drivers 40420 from an unfired position (FIG. 18) to a fired position during the firing stroke. After the firing stroke is completed, one or more of the staple drivers 40420 may move, or fall, from their fired positions toward their unfired positions, as depicted in FIG. 19. Depending on various circumstances, the staple drivers 40420 may move various amounts toward their unfired position after the firing stroke is completed depending on, among other things, the fit of the driver 40420 within its corresponding staple cavity 40407. As such, one or more drivers 40420 may only drop slightly whereas other drivers 40420 may drop entirely into their unfired positions.

Figure 20:
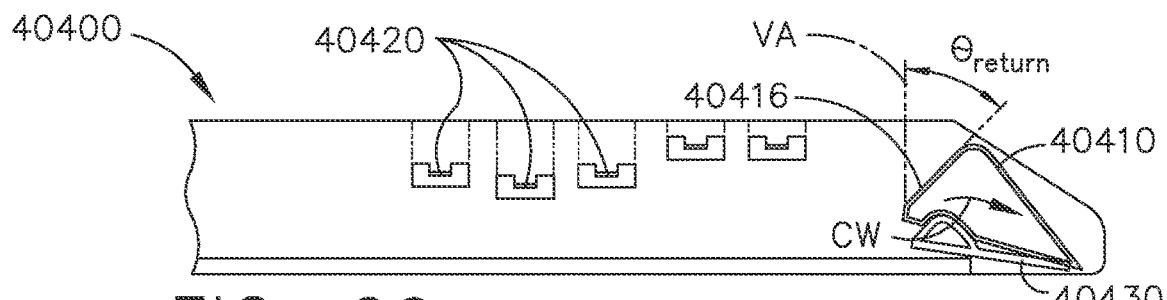
FIG. 20 is a partial cross-sectional view of the staple cartridge of FIG. 18 depicting the sled assembly in a distal fired position.
Figure 21:
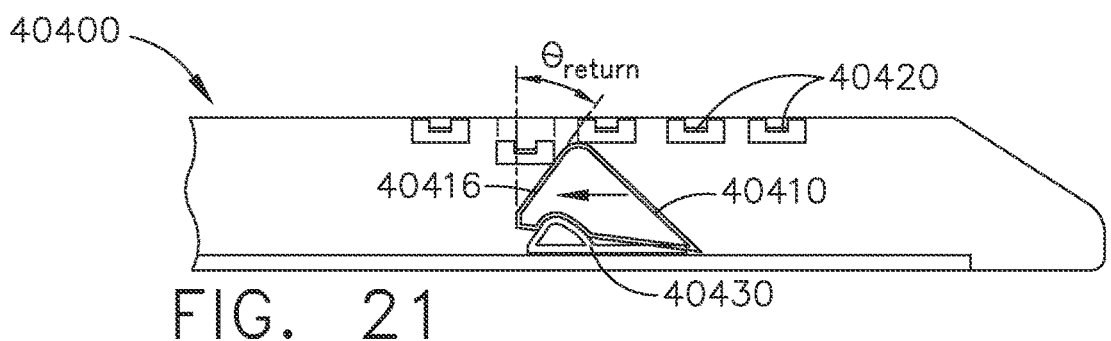
FIG. 21 is a partial cross-sectional view of the staple cartridge of FIG. 18 depicting the sled assembly retracted proximally from the distal fired position.

During the firing stroke, as discussed above, the sled 40410 is moved distally toward the distal end of the staple cartridge 40400. Notably, the sled lift cam 40430 does not travel distally with the sled 40410. Also notably, the proximal ramps 40416 of the sled 40410 are oriented at an angle $\theta_{advance}$ relative to vertical axis VA. As the sled 40410 approaches the distal fired position, the cutout region 40415 of the sled 40410 at least partially receives the sled lift cam 40430 therein as illustrated in FIG. 20. Specifically, the distal end of the advancing sled 40410 rides up and over proximal ramps 40433 of the sled lift cam 40430 until the sled lift cam 40430 is received in the cutout region 40415 of the sled 40410. A proximal protrusion 40432 of the sled lift cam 40430 can be received in the cutout region 40415 of the sled 40410 beneath the driver lift cam 40418. Notably, at least a portion of the sled lift cam 40430 is vertically larger than cutout region 40415 of the sled 40410 in which it is received. As such, the orientation of the sled 40410 is changed, i.e. the sled 40410 is rotated in direction CW, when the sled 40410 receives the sled lift cam 40430.

During the retraction stroke of the sled 40410, the sled lift cam 40430 remains engaged with the sled 40410 and the proximal ramps 40416 of the sled are oriented at angle $\theta_{return}$ relative to the vertical axis VA. Further, referring primarily to FIGS. 19 and 20, angle $\theta_{return}$ is greater than angle $\theta_{advance}$. As such, the proximal ramps 40416 of the sled 40410 have a more gradual slope relative to the vertical axis VA during the retraction stroke as compared to during the firing stroke. The proximal ramps 40416 of the sled 40410 are configured to interact with fallen staple drivers 40420 at angle $\theta_{return}$ as comparted angle $\theta_{advance}$ which is steeper than $\theta_{return}$. The more gradual slope of the proximal ramps 40416 during the retraction stroke may be advantageous in lifting dropped staple drivers 40420, for example. Moreover, utilizing the sled lift cam 40430 to change the angle of the proximal ramps 40416 during the retraction stroke creates a compact assembly.

Figure 23:
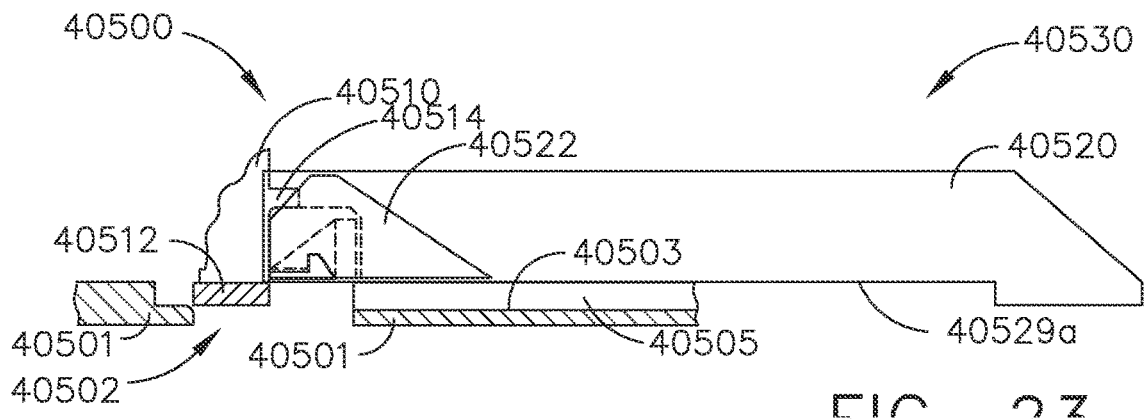
FIG. 23 is a partial cross-sectional view of a surgical instrument comprising an end effector and a firing driver depicting a staple cartridge received in the end effector and a sled of the staple cartridge in a proximal unfired position in accordance with the present disclosure.
Figure 24:
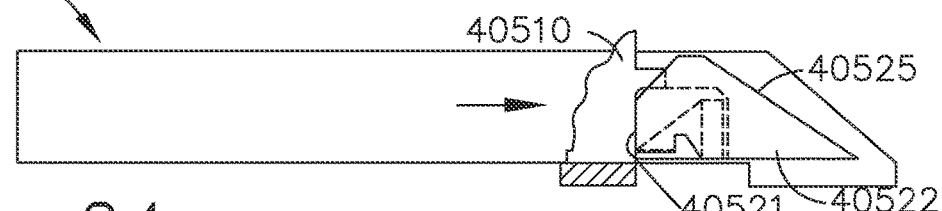
FIG. 24 is a partial cross-sectional view of the surgical instrument of FIG. 23 depicting the sled advanced to a distal fired position by the firing driver.

FIGS. 23-26 illustrate a surgical instrument 40500 comprising an end effector 40530 and a firing driver 40510 movable within the end effector 40530. The end effector 40530 comprises a first jaw 40501 and a second jaw movable relative to the first jaw 40501 to capture tissue in between the first jaw 40501 and the second jaw. The first jaw 40501 may be movable relative to the second jaw. The first jaw 40501 is configured to receive a staple cartridge 40520 therein as illustrated in FIG. 23. The staple cartridge 40520 comprises staple drivers, such as those discussed herein, and a sled 40522 configured to move distally to engage the staple drivers and eject staples from the staple cartridge 40520 during a staple firing stroke. The staple cartridge 40520 can be configured to be inserted into the first jaw 40501 with the sled 40522 in a proximal unfired position and the firing driver 40510 positioned proximal to the sled 40522. The firing driver 40510 is then distally advanced toward the sled 40522 after the staple cartridge 40520 is inserted into the first jaw 40501 and defeats a firing lockout, as discussed in greater detail below.

When the staple cartridge 40520 is seated in the first jaw 40501, as illustrated in FIG. 23, a longitudinal cavity, or gap, 40505 exists between the first jaw 40501 and the staple cartridge 40520. The longitudinal cavity 40505 is defined by a bottom surface 40529a of the staple cartridge 40520 and a top surface 40503 of the first jaw 40501. The staple cartridge 40520 is attached or affixed to the first jaw 40501 such that the bottom surface 40529a of the staple cartridge 40520 is vertically spaced apart from the top surface 40503 of the first jaw 40501 to create the longitudinal cavity 40505. However, the longitudinal cavity 40505 may be defined entirely within the first jaw 40501, for example.

Further to the above, the firing driver 40510 comprises a lower laterally extending foot 40512 configured to move within the longitudinal cavity 40505 during a staple firing stroke and a retraction stroke. The firing driver 40510 further comprises a flexible tab 40516 and a nose 40514 extending distally from the firing driver 40510. The firing driver 40510 is biased toward the first jaw 40501 by a biasing member, such as a spring, for example, positioned against a top surface of the firing driver 40510.

When the staple cartridge 40520 is seated in the first jaw 40501 and sled 40522 of the staple cartridge 40520 is in its proximal unfired position, as illustrated in FIG. 23, and the firing driver 40510 is advanced distally to perform a staple firing stroke, the nose 40514 of the firing driver 40510 rests on a ledge 40523 of the sled 40522 to prevent the foot 40512 of the firing driver 40510 from entering a lockout opening 40502 in the first jaw 40501. If, however, the firing driver 40510 is advanced distally without the staple cartridge 40520 being seated in the first jaw 40501, or advanced distally when the staple cartridge 40520 is seated in the first jaw 40501 but the sled 40522 is not in its proximal unfired position at the outset of the staple firing stroke, the nose 40514 of the firing driver 40510 will not be supported by the ledge 40523 of the sled 40522 and the firing driver 40510 will be biased into the lockout opening 40502 by the biasing member and is, as a result, prevented from being advanced through the staple firing stroke. This arrangement provides a missing cartridge lockout as well as a spent cartridge lockout. Once the missing cartridge/spent cartridge lockout has been overcome by seating an unspent staple cartridge 40520 in the first jaw 40501 and the firing driver 40510 is moved distally to perform the staple firing stroke, the flexible tab 40516 of the firing driver 40510 is received in a recess 40529 of the sled 40522 to operably couple the firing driver 40510 and the sled 40522, as discussed in greater detail below.

The sled 40522 comprises a first portion 40524 and a second portion 40526 housed within the first portion 40524. The second portion 40526 is slidably attached to the first portion 40524 such that the second portion 40526 is movable relative to the first portion 40524. The second portion 40526 may comprise a protrusion that extends into a longitudinal slot of the first portion 40524 to slidably couple the first portion 40524 and the second portion 40526. Other attachment methods are contemplated for slidably attaching the first portion 40524 and the second portion 40526 together. The first portion 40524 comprises at least one distal ramp 40525 facing distally that is configured to engage the staple drivers of the staple cartridge 40520 during the firing stroke. The first portion 40524 further comprises a first proximal ramp 40527 facing proximally. The second portion 40526 comprises the recess 40529 discussed above and a second proximal ramp 40528. The sled 40522 further comprises a knife, or tissue cutting member, such as a knife 40316, for example. That said, the sled 40522 may not comprise a knife or tissue cutting member.

Figure 25:
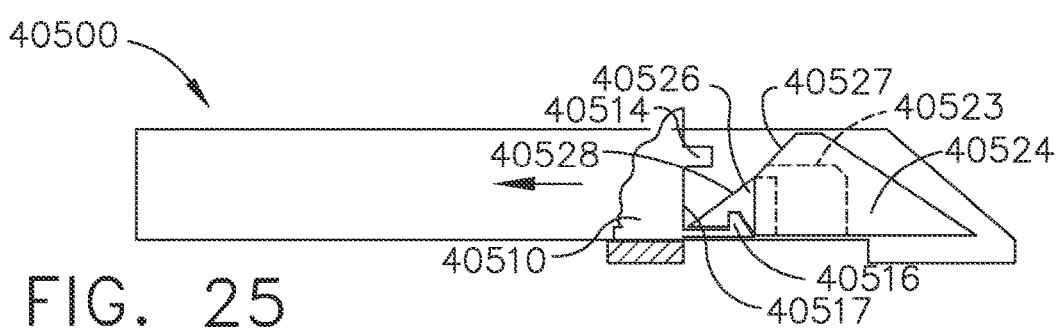
FIG. 25 is a partial cross-sectional view of the surgical instrument of FIG. 23 depicting a portion of the retraction stroke where the firing driver is retracted and the sled is expanded.
Figure 26:
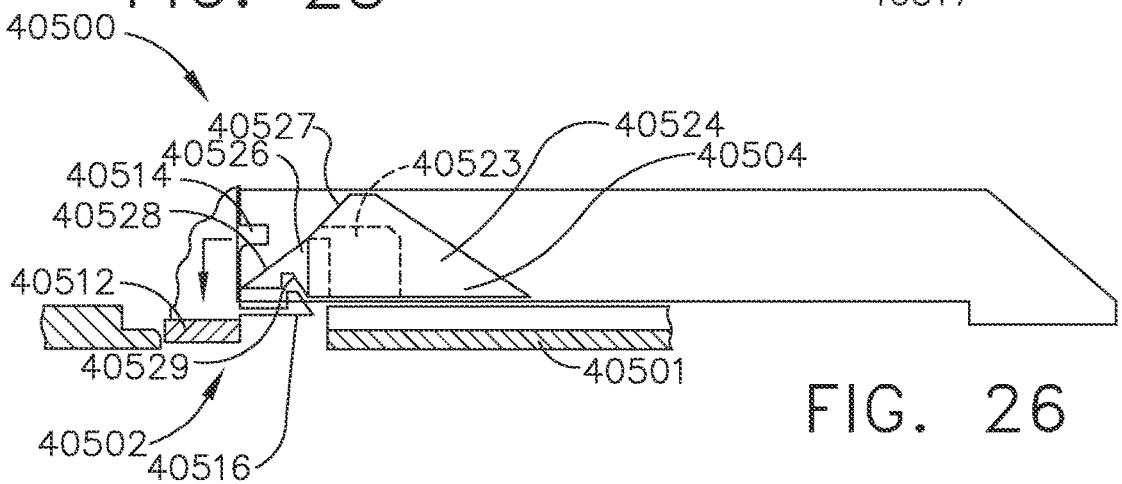
FIG. 26 is a partial cross-sectional view of the surgical instrument of FIG. 23 depicting the firing driver disengaging the expanded sled and entering a lockout opening of the end effector upon retraction.

As discussed above, the firing driver 40510 is advanced distally to engage the sled 40522. Specifically, a distal end 40517 of the firing driver 40510 abuts a proximal end 40521 of the second portion 40526 to advance the sled 40522 distally as the firing driver 40510 is advanced distally by a firing drive. When the firing driver 40510 is advanced from the position in FIG. 23 to the position in FIG. 24 during a staple firing stroke, the distal ramp 40525 of the sled 40522 engages the staple drivers to eject the staples from the staple cartridge 40520. After the firing stroke has been completed, or at least partially completed, the firing driver 40510 is retracted in the proximal direction from the position in FIG. 24 to the position in FIG. 25 during a retraction stroke. When the firing driver 40510 moves from the position in FIG. 24 to the position in FIG. 25, the second portion 40526 of the sled 40522 is pulled proximally relative to the first portion 40524 of the sled 40522 to transition the sled 40522 from a collapsed configuration (FIG. 24) to an expanded configuration (FIG. 25). Specifically, the flex tab 40516 of the firing driver 40510 is engaged with the recess 40529 of the second portion 40526 of the sled 40522 such that when the firing driver 40510 is pulled proximally, the second portion 40526 is pulled proximally relative to the first portion 40524. Once the second portion 40526 is completely expanded relative to the first portion 40524, the first and second portions 40524, 40526 are pulled proximally together by the firing driver 40510 to complete the retraction stroke.

Further to the above, the second proximal ramp 40528 of the second portion 40526 is exposed when the sled 40522 is in its expanded configuration as illustrated in FIG. 25. The second proximal ramp 40528 is configured to work in conjunction with the first proximal ramp 40527 of the first portion 40524 to engage the staple drivers that have fallen down from their fired positions. Specifically, the proximal ramps 40527, 40528 are configured to cammingly engage and lift one or more of the staple drivers which may be in the way of the sled 40522 during the retraction stroke to permit the sled 40522 to complete the retraction stroke.

Further to the above, when the sled 40522 is transitioned from the collapsed configuration (FIG. 24) to the expanded configuration (FIG. 25), the distal nose portion 40514 of the firing driver 40510 no longer rests on the ledge 40523 of the sled 40522. As such, when the sled 40522 is retracted to the position illustrated in FIG. 26, the foot 40512 of the firing driver 40510 is biased into the lockout opening 40502 by the biasing member. As such, the firing driver 40510 is prevented from advancing the sled 40522 again if the spent staple cartridge 40520 remains positioned in the first jaw 40501. Further, when the sled 40522 is in the proximal unfired position depicted in FIG. 26, the second portion 40526 of the sled 40522 is visible to a user of the surgical instrument 40500 through the lockout opening 40502 to indicate to the user that the staple cartridge 40520 has been fired, or at least partially fired. After the retraction stroke has been completed, the now-spent 40520 staple cartridge can be removed from the first jaw 40501. After the staple cartridge 40520 is removed from the first jaw 40501, the locked out firing driver 40510 is prevented from being advanced distally through another staple firing stroke unless an unfired staple cartridge 40520—with the sled 40522 in the proximal unfired position—is installed into the first jaw 40501. An unfired staple cartridge 40520 can be inserted into the first jaw 40501 at an angle such that the ledge 40523 of the sled 40522 engages the distal nose 40514 of the firing driver 40510 to lift the firing driver 40510 out of the lockout opening 40502 which, as discussed above, defeats the missing cartridge/firing cartridge lockout and permit the firing driver 40510 to be advanced distally through another staple firing stroke.

During the retraction stroke of the firing driver 40510, referring again to FIG. 26, the first portion 40524 of the sled 40522 will not retract proximally all the way to its original proximal unfired position (i.e., the position in FIG. 23 when the staple cartridge 40520 was seated in the first jaw 40501). Specifically, the sled 40522 is retracted to a proximal returned position illustrated in FIG. 26 during the retraction stroke. The proximal returned position of the sled 40522 is distal to the proximal unfired position of the sled 40522. As such, if the spent staple cartridge 40520 with the sled 40522 in the position of FIG. 26 (i.e., the proximal returned position) is not removed from the end effector 40530, or is removed and re-inserted, the ledge 40523 of the sled 40522 will not be positioned proximal enough in the first jaw 40501 to defeat the lockout discussed above.

Figure 27:
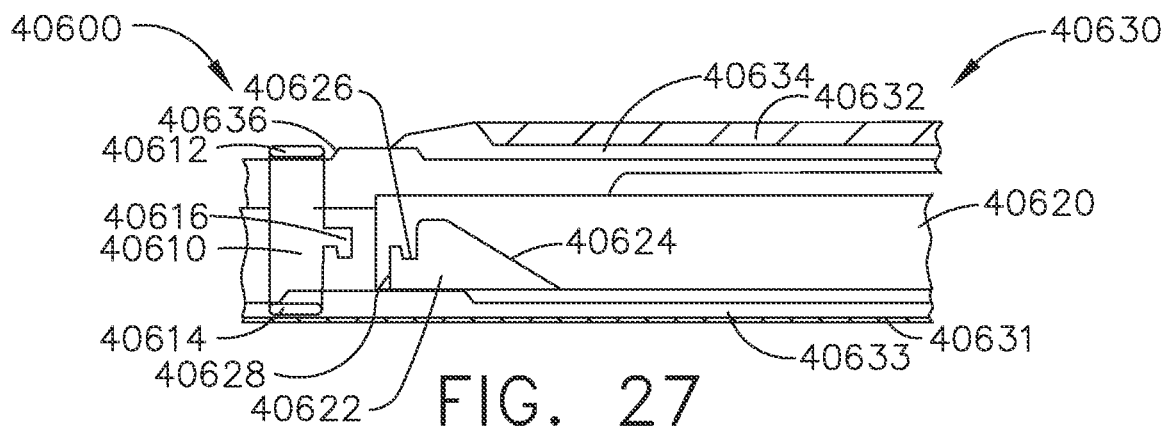
FIG. 27 is a partial cross-sectional view of a surgical instrument comprising an end effector and a firing driver depicting a staple cartridge received in the end effector with a sled of the staple cartridge in an unfired position and the firing driver in a proximal position in accordance with the present disclosure.
Figure 28:
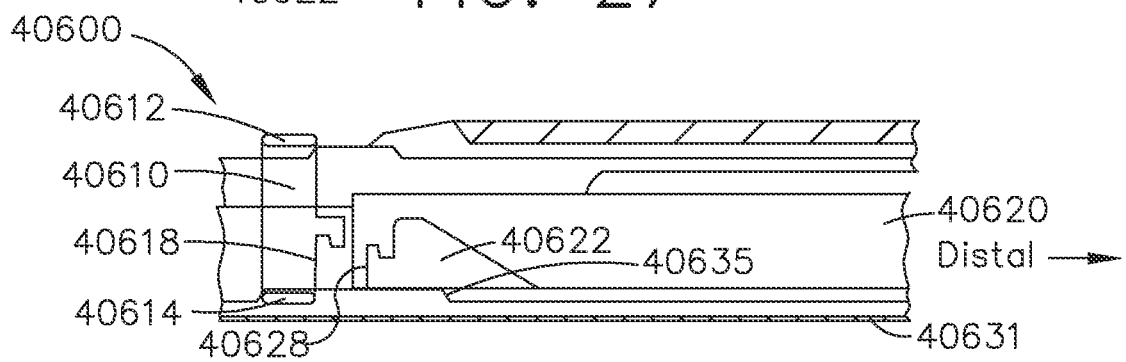
FIG. 28 is a partial cross-sectional view of the surgical instrument of FIG. 27 depicting the firing driver advanced from the proximal position toward the staple cartridge.
Figure 29:
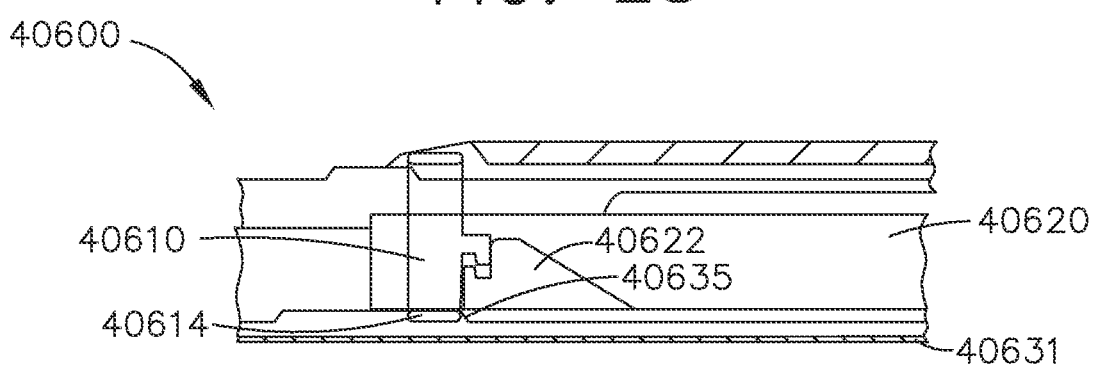
FIG. 29 is a partial cross-sectional view of the surgical instrument of FIG. 27 depicting the firing driver engaged with the sled of the staple cartridge.
Figure 30:
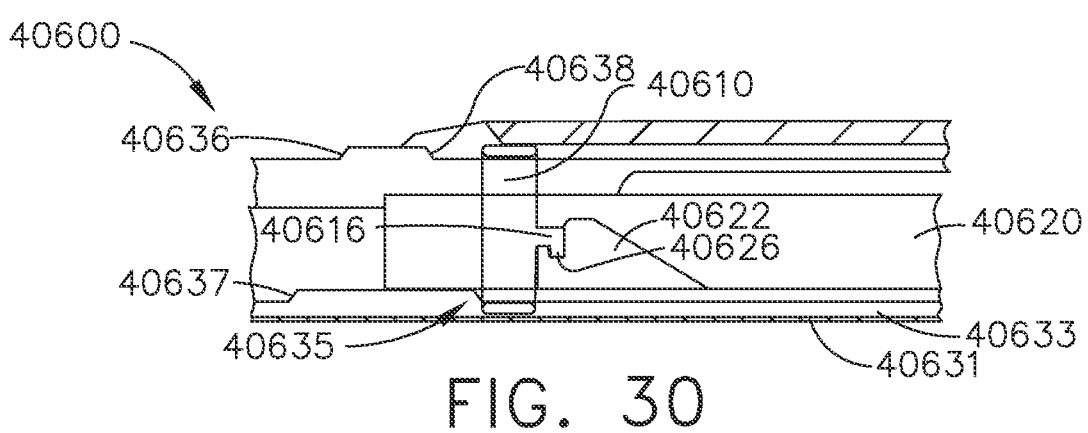
FIG. 30 is a partial cross-sectional view of the surgical instrument of FIG. 27 depicting the firing driver operably coupled to the sled of the staple cartridge.

FIGS. 27-34 illustrate a surgical instrument 40600 comprising a firing driver 40610 and an end effector 40630 configured to receive a staple cartridge 40620. The firing driver 40610 is configured to move relative to the end effector 40630. The end effector 40630 comprises a first jaw 40631 and a second jaw 40632 movable relative to the first jaw 40631 to capture tissue in between the first jaw 40631 and the second jaw 40632. The first jaw 40631 can be movable relative to the second jaw 40632. The staple cartridge 40620 comprises a plurality of staple drivers, such as those described herein, and a sled 40622 movable distally by the firing driver 40610 to eject staples from the staple cartridge 40620 during a staple firing stroke. The sled 40622 comprises at least one distal ramp 40624 configured to cammingly engage the staple drivers to eject the staples. The sled 40622 may comprise a cutting member, such as a knife, for example, configured to incise patient tissue captured between the first jaw 40631 and the second jaw 40632. However, the firing driver 40610 may comprise the cutting member instead of the sled 40622. Further, FIG. 27 illustrates the first jaw 40631 and the second jaw 40632 in a closed configuration with the sled 40622 of the staple cartridge 40620 in an unfired position and the firing driver 40610 in a proximal position after the staple cartridge 40620 has been inserted into the first jaw 40631. The firing driver 40610 comprises a first lateral cam portion 40614 configured to engage the first jaw 40631 and a second lateral cam portion 40612 configured to engage the second jaw 40632 during the staple firing stroke, as discussed in greater detail below.

The first jaw 40631 of the end effector 40630 comprises a longitudinal cavity 40633 defined therein that is configured to receive the first cam 40614 of the firing driver 40610. Further, the second jaw 40632 comprises a longitudinal cavity 40634 defined therein that is configured to receive the second cam 40612 of the firing driver 40610. The first jaw 40631 comprises a proximal ramp portion 40637 and a distal ramp 40635 defined by the longitudinal cavity 40633 of the first jaw 40631. Similarly, the second jaw 40632 comprises a proximal ramp 40636 and a distal ramp 40638 defined by the longitudinal cavity 40634 of the second jaw 40632. At the outset of the staple firing stroke, the ramps 40635, 40637, 40636, 40638 of the first and second jaws 40631, 40632 move the firing driver 40610 up and down relative to the staple cartridge 40620 to engage the firing driver 40610 with the sled 40622 of the staple cartridge 40620, as discussed in greater detail below. Moreover, as discussed in greater detail below, the ramps 40635, 40637, 40636, 40638 of the first and second jaws 40631, 40632 move the firing driver 40610 up and down relative to the staple cartridge 40620 during the retraction stroke to disengage the firing driver 40610 from the sled 40622

Further to the above, the sled 40622 is presented in front of the firing driver 40610 when the staple cartridge 40620 is seated in the first jaw 40631, as depicted in FIG. 27. When the firing driver 40610 is initially advanced distally, i.e., from the position in FIG. 27 to the position in FIG. 28, the second cam 40612 engages the proximal ramp 40636 of the second jaw 40632 which lifts the firing driver 40610 upwardly away from the first jaw 40631. As the firing driver 40610 advances further distally from the position in FIG. 28 to the position in FIG. 29, a distal face 40618 of the firing driver 40610 engages a proximal face 40628 of the sled 40622 to advance the sled 40622. As the firing driver 40610 advances from the position in FIG. 29 to the position in FIG. 30, the first cam 40614 of the firing driver 40610 engages the distal ramp 40635 of the first jaw 40631 which drives the firing driver 40610 downward toward the first jaw 40631. Moreover, a distal hook portion 40616 of the firing driver 40610 engages a recess 40626 of the sled 40622 to operably couple the firing driver 40610 and the sled 40622 as the firing driver 40610 moves from the position in FIG. 29 to the position in FIG. 30. At such point, the firing driver 40610 is movable distally to advance the sled 40622 to the distal end of the staple cartridge 40620 during a staple firing stroke to eject the staples from the staple cartridge 40620.

Figure 31:
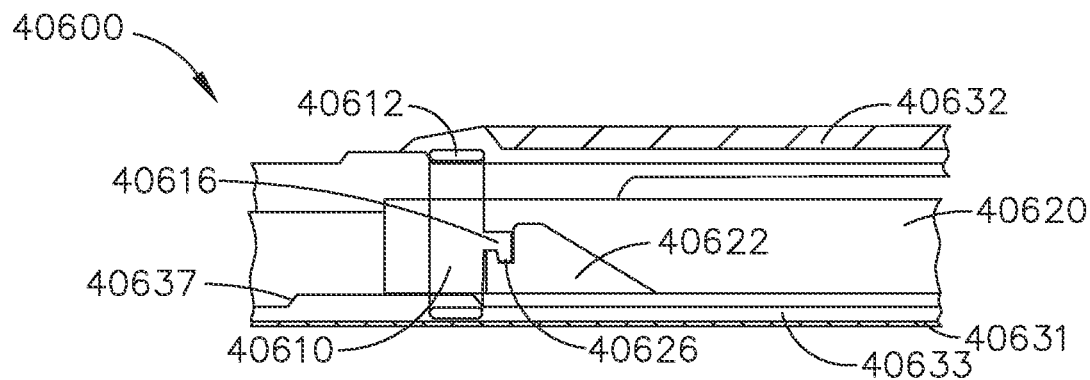
FIG. 31 is a partial cross-sectional view of the surgical instrument of FIG. 27, depicting the firing driver and sled retracted proximally during a retraction stroke after the firing stroke is completed.
Figure 32:
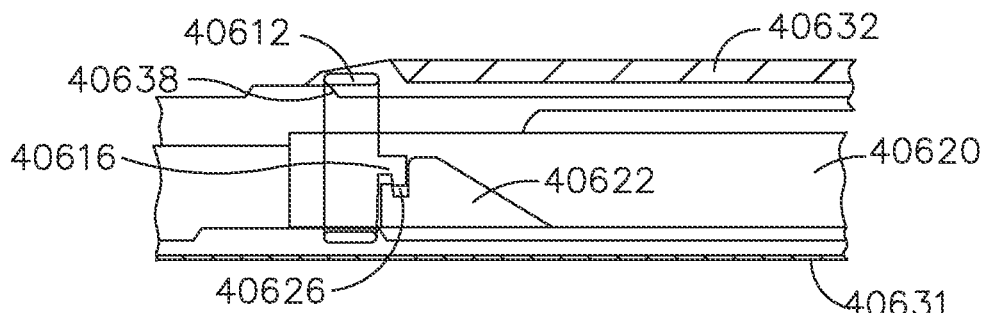
FIG. 32 is a partial cross-sectional view of the surgical instrument of FIG. 27 depicting the firing driver operably de-coupled from the sled of the staple cartridge.

After the firing stroke is completed, further to the above, the firing driver 40610 is configured to retract the sled 40622 from its fired position at the distal end of the staple cartridge 40620 to the position in FIG. 31 during a retraction stroke. The sled 40622 is pulled proximally by the firing driver 40610 during the retraction stroke due to the engagement of the distal hook 40616 of the firing driver 40610 with the recess 40626 of the sled 40622. As the firing driver 40610 is retracted proximally from the position in FIG. 31 to the position in FIG. 32, a distal ramp 40638 of the second jaw 40632 drives the firing driver 40610 upward away from the first jaw 40631 and disengages the distal hook 40616 of the firing driver 40610 from the recess 40626 in the sled 40622. The sled 40622 may be constrained to only longitudinal movement within the staple cartridge 40620 such that, when the firing driver 40610 is driven upwardly, the sled 40622 remains stationary in the vertical direction. As the firing driver 40610 is retracted proximally from the position in FIG. 32 to the position in FIG. 33, the sled 40622 is not retracted and remains stationary. As the firing driver 40610 is retracted from the position in FIG. 33 to the position in FIG. 34, the first cam 40614 of the firing driver 40610 engages a proximal ramp 40637 of the first jaw 40631 which drives the firing driver 40610 downward away from the second jaw 40632. FIG. 34 illustrates the firing driver 40610 in the same proximal position as in FIG. 27. The spent staple cartridge 40620 can be removed from the end effector 40630 when the firing driver 40610 is in either of the positions depicted in FIG. 33 or FIG. 34, for example. If another staple cartridge 40620, i.e., an unspent staple cartridge 40620, is seated in the first jaw 40631—with the sled 40622 of the new staple cartridge 40620 in its unfired position—the firing driver 40610 can be advanced distally in the manner described above to complete another staple firing stroke. If, however, the firing driver 40610 is advanced distally without an unspent staple cartridge 40620 seated in the first jaw 40631—with the sled 40622 in its unfired position—the firing driver 40610 is stopped by a missing cartridge/spent cartridge lockout.

Figure 33:
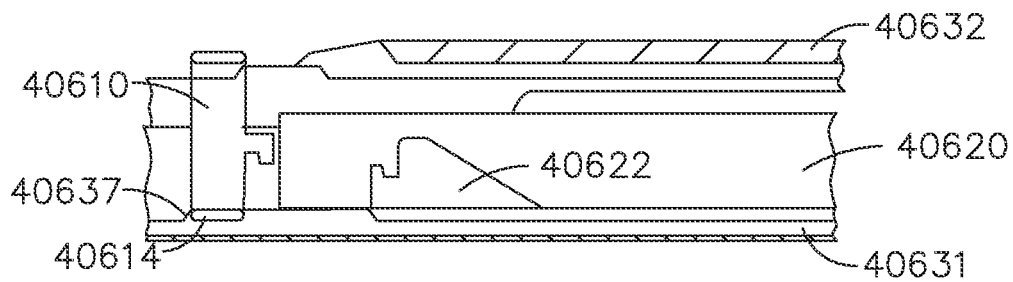
FIG. 33 is a partial cross-sectional view of the surgical instrument of FIG. 27 depicting the firing driver retracted proximal to the sled after the firing driver is de-coupled from the sled.
Figure 34:
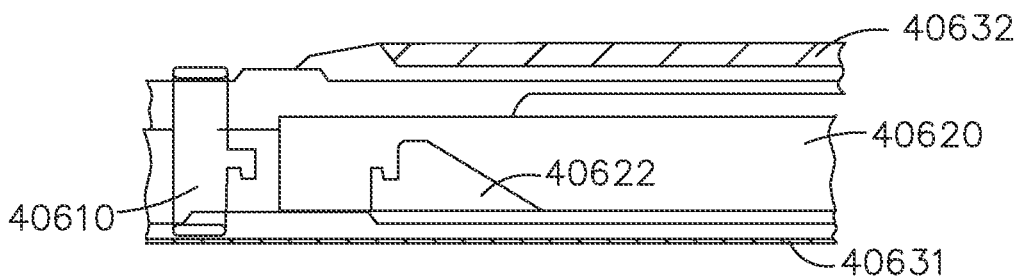
FIG. 34 is a partial cross-sectional view of the surgical instrument of FIG. 27 depicting the firing driver retracted to the proximal position.

Further to the above, after the retraction stroke, the sled 40622 is in a more distal position in FIGS. 33 and 34 than the initial unfired position of the sled 40622 illustrated in FIG. 27. As such, if the spent staple cartridge 40620 with the sled 40622 in the position of FIG. 33 is not removed from the end effector 40630, or is removed and re-inserted, the firing driver 40610 will not be able to properly couple with the sled 40622.

Various aspects of the subject matter described herein are set out in the following examples.

Example 1—A staple cartridge for use with a surgical instrument. The staple cartridge comprises a cartridge body (40101), a staple (40150), a staple driver (40120), and a sled (40310). The cartridge body (40101) comprises a deck (40102), a longitudinal slot (40103), and a staple cavity (40105) defined in the deck (40102). The deck includes a proximal end and a distal end. The longitudinal slot (40103) extends from the proximal end toward the distal end. The staple (40150) is removably stored in the staple cavity (40105). The staple driver (40120) is movably positioned in the staple cavity (40105). The sled (40310) is movable from a proximal position to a distal position during a firing stroke. The sled (40310) is movable from the distal position toward the proximal position during a retraction stroke. The sled (40310) comprises a base (40313), a central portion (40314) configured to move within the longitudinal slot (40103), a first rail (40312), a second rail (40312), and a driver lift cam (40318). The first rail (40312) is positioned on a first side of the central portion (40314). The first rail (40312) comprises a first distal-facing ramp (40315). The second rail (40312) is positioned on the first side of the central portion (40314). The second rail (40312) comprises a second distal-facing ramp (40315). The first distal-facing ramp (40315) and the second distal-facing ramp (40315) are configured to engage and move the staple driver (40120) from an unfired position to a fired position during the firing stroke. The driver lift cam (40318) is positioned intermediate the first rail (40312) and the second rail (40312). The driver lift cam (40318) is configured to engage the staple driver (40120) and move the staple driver (40120) toward the fired position during the retraction stroke.

Example 2—The staple cartridge of Example 1, wherein the driver lift cam (40318) comprises an arcuate protrusion extending upwardly from the base.

Example 3—The staple cartridge of Examples 1 or 2, wherein the sled (40310) comprises a knife (40316) movable within the longitudinal slot (40103).

Example 4—The staple cartridge of Examples 1, 2, or 3, wherein the staple cartridge comprises a proximal knife housing (40104) configured to store the knife (40316) when the sled (40310) is in the proximal position.

Example 5—The staple cartridge of Examples 1, 2, 3, or 4, wherein the staple driver (40120) comprises a staple support (40122) configured to support the staple (40105) thereon, a distal ramp (40121), and a distal camming surface (40127*a*, 40127*b*).

Example 6—The staple cartridge of Example 5, wherein the driver lift cam (40318) of the sled (40310) is configured to engage the distal ramp (40121) of the staple driver (40120) during the retraction stroke to lift the staple driver (40120) from the unfired position to an intermediate position, and wherein the intermediate position is intermediate the unfired position and the fired position.

Example 7—The staple cartridge of Example 6, wherein at least one of the first rail (40312) and the second rail (40312) of the sled (40310) comprises a proximal-facing ramp (40317) configured to engage the distal camming surface (40127*a*, 40127*b*) of the staple driver (40120) during the retraction stroke to move the staple driver (40120) from the intermediate position to the fired position.

Example 8—The staple cartridge of Example 7, wherein the distal-facing ramp (40315) of the sled (40310) is defined by a first angle, wherein the proximal-facing ramp (40317) of the sled (40310) is defined by a second angle, and wherein the second angle is steeper than the first angle.

Example 9—The staple cartridge of Examples 7 or 8, wherein the proximal-facing ramp (40317) of the sled (40310) is steeper than the distal-facing ramp (40315) of the sled (40310).

Example 10—The staple cartridge of Examples 1, 2, 3, 4, 5, 6, 7, 8, or 9, wherein the driver lift cam (40318) of the sled (40310) is configured to move the staple driver (40120) a minimum distance toward its fired position during the retraction stroke of the sled (40310), and wherein the minimum distance is at least half of the overall height of the staple driver (40120).

Example 11—The staple cartridge of Examples 1, 2, 3, 4, 5, 6, 7, 8, 9, or 10, wherein the driver lift cam (40318) of the sled (40310) is configured to lift the staple driver (40120) a first distance toward its fired position during the retraction stroke of the sled (40310), and wherein at least one of the first rail (40312) and the second rail (40312) of the sled (40310) comprises a proximal-facing ramp (40317) configured to engage the staple driver (40120) during the retraction stroke to lift the staple driver (40120) a second distance toward the fired position during the retraction stroke of the sled (40310).

Example 12—A surgical instrument comprising an end effector (40530), a firing driver (40510), and a staple cartridge (40520) seated in the end effector (40530). The firing driver (40510) is movable relative to the end effector (40510) from a proximal position to a distal position during a firing stroke and from the distal position to the proximal position during a retraction stroke. The staple cartridge (40520) comprises a cartridge body (40101), a staple (40150), a staple driver (40120), and a sled (40522). The cartridge body (40101) comprises a deck (40102), a longitudinal slot (40103), and a staple cavity (40105) defined in the deck (40102). The deck (40102) includes a proximal end and a distal end. The longitudinal slot (40103) extends from the proximal end toward the distal end. The staple (40150) is removably stored in the staple cavity (40105). The staple driver (40120) is movably positioned in the staple cavity (40105). The sled (40522) is movable distally from an unfired position to a fired position by the firing driver (40510) during the firing stroke. The sled (40522) is movable proximally from the fired position to a returned position by the firing driver (40510) during the retraction stroke. The sled (40522) comprises a first sled component (40524) and a second sled component (40526). The first sled component (40524) comprises a distal-facing ramp (40525) configured to engage and move the staple driver (40120) from an unfired position to a fired position during the firing stroke. The second sled component (40526) is movable relative to the first sled component (40524). The second sled component (40526) comprises a proximal-facing ramp (40528). The sled (40522) is configurable in a collapsed configuration and an expanded configuration. At least a portion of the proximal-facing ramp (40528) is nested within the first sled component (40524) when the sled (40522) is in the collapsed configuration. The sled (40522) is in the collapsed configuration during the firing stroke. The sled (40522) is in the expanded configuration during the retraction stroke. At least a portion of the proximal-facing ramp (40528) extends proximally relative to the first sled component (40524) when the sled (40522) is in the expanded configuration. The proximal-facing ramp (40528) is configured to engage and move the staple driver (40120) toward the fired position during the retraction stroke.

Example 13—The surgical instrument of Example 12, wherein the returned position of the sled (40522) is distal to the unfired position of the sled (40522).

Example 14—The surgical instrument of Examples 12 or 13, wherein the end effector (40530) comprises a lockout opening (40502), and wherein the proximal-facing ramp (40528) extends over at least a portion of the lockout opening (40502) when the sled (40522) is in the returned position.

Example 15—The surgical instrument of Example 14, wherein the firing driver (40510) enters the lockout opening (40502) upon the completion of the retraction stroke.

Example 16—A staple cartridge for use with a surgical instrument. The staple cartridge comprises a cartridge body, a staple, a staple driver, and a sled. The cartridge body comprises a deck, a longitudinal slot, and a staple cavity defined in the deck. The deck includes a proximal end and a distal end. The longitudinal slot extends from the proximal end toward the distal end. The staple is removably stored in the staple cavity. The staple driver is movably positioned in the staple cavity. The sled is movable from a proximal position to a distal position during a firing stroke. The sled is movable from the distal position toward the proximal position during a retraction stroke. The sled comprises a base, a central portion configured to move within the longitudinal slot, a first rail, a second rail, and a driver lift cam. The first rail is positioned on a first side of the central portion. The first rail comprises a first distal-facing ramp. The second rail is positioned on the first side of the central portion. The second rail comprises a second distal-facing ramp. The first distal-facing ramp and the second distal-facing ramp are configured to engage and move the staple driver from an unfired position to a fired position during the firing stroke. The driver lift cam is positioned intermediate the first rail and the second rail. The driver lift cam is configured to engage the staple driver and move the staple driver toward the fired position during the retraction stroke.

Example 17—The staple cartridge of Example 16, wherein the driver lift cam comprises an arcuate protrusion extending upwardly from the base.

Example 18—The staple cartridge of Examples 16 or 17, wherein the sled comprises a knife movable within the longitudinal slot.

Example 19—The staple cartridge of Examples 16, 17, or 18, wherein the staple cartridge comprises a proximal knife housing configured to store the knife when the sled is in the proximal position.

Example 20—The staple cartridge of Examples 16, 17, 18, or 19, wherein the staple driver comprises a staple support configured to support the staple thereon, a distal ramp, and a distal camming surface.

Example 21—The staple cartridge of Example 20, wherein the driver lift cam of the sled is configured to engage the distal ramp of the staple driver during the retraction stroke to lift the staple driver from the unfired position to an intermediate position, and wherein the intermediate position is intermediate the unfired position and the fired position.

Example 22—The staple cartridge of Example 21, wherein at least one of the first rail and the second rail of the sled comprises a proximal-facing ramp configured to engage the distal camming surface of the staple driver during the retraction stroke to move the staple driver from the intermediate position to the fired position.

Example 23—The staple cartridge of Examples 16, 17, 18, 19, 20, 21, or 22, wherein the driver lift cam of the sled is configured to lift the staple driver a first distance toward its fired position during the retraction stroke of the sled, and wherein at least one of the first rail and the second rail of the sled comprises a proximal-facing ramp configured to engage the staple driver during the retraction stroke to lift the staple driver a second distance toward the fired position during the retraction stroke of the sled.

Example 24—The staple cartridge of Examples 16, 17, 18, 19, 20, 21, 22, or 23, wherein the first rail defines a first plane and the second rail defines a second plane, and wherein the driver lift cam is positioned intermediate the first plane and the second plane.

Example 25—The staple cartridge of Example 24, wherein the staple driver comprises a staple support configured to support the staple thereon, a distal ramp on the staple support, and a proximal camming surface aligned with the first plane or the second plane. The driver lift cam is aligned with the distal ramp.

Example 26—The staple cartridge of Examples 24 or 25, wherein the distal ramp on the staple driver is not aligned with the first plane or the second plane.

Example 27—A surgical instrument comprising an end effector, a firing driver, and a staple cartridge seated in the end effector is disclosed. The firing driver is movable relative to the end effector from a proximal position to a distal position during a firing stroke and from the distal position to the proximal position during a retraction stroke. The staple cartridge comprises a cartridge body, a staple, a staple driver, and a sled. The cartridge body comprises a deck, a longitudinal slot, and a staple cavity defined in the deck. The deck includes a proximal end and a distal end. The longitudinal slot extends from the proximal end toward the distal end. The staple is removably stored in the staple cavity. The staple driver is movably positioned in the staple cavity. The sled is movable distally from an unfired position to a fired position by the firing driver during the firing stroke. The sled is movable proximally from the fired position to a returned position by the firing driver during the retraction stroke. The sled comprises a first sled component and a second sled component. The first sled component comprises a distal-facing ramp configured to engage and move the staple driver from an unfired position to a fired position during the firing stroke. The second sled component is movable relative to the first sled component. The second sled component comprises a proximal-facing ramp. The sled is configurable in a collapsed configuration and an expanded configuration. At least a portion of the proximal-facing ramp is nested within the first sled component when the sled is in the collapsed configuration. The sled is in the collapsed configuration during the firing stroke. The sled is in the expanded configuration during the retraction stroke. At least a portion of the proximal-facing ramp extends proximally relative to the first sled component when the sled is in the expanded configuration. The proximal-facing ramp is configured to engage and move the staple driver toward the fired position during the retraction stroke.

Example 28—The surgical instrument of Example 27, wherein the returned position of the sled is distal to the unfired position of the sled.

Example 29—The surgical instrument of Examples 27 or 28, wherein the end effector comprises a lockout opening, and wherein the proximal-facing ramp extends over at least a portion of the lockout opening when the sled is in the returned position.

Example 30—The surgical instrument of Example 29, wherein the firing driver enters the lockout opening upon the completion of the retraction stroke.

Example 31—The surgical instrument of Examples 27, 28, 29, or 30, wherein the sled comprises a knife movable within the longitudinal slot.

Example 32—The surgical instrument of Examples 27, 28, 29, 30, or 31, wherein the staple cartridge is replaceable.

Example 33—A staple cartridge for use with a surgical instrument. The staple cartridge comprises a cartridge body, a staple, a staple driver, and a sled. The cartridge body comprises a deck, a longitudinal slot, and a staple cavity defined in the deck. The deck includes a proximal end and a distal end. The longitudinal slot extends from the proximal end toward the distal end. The longitudinal slot defines a longitudinal axis. The staple is removably stored in the staple cavity. The staple driver is movably positioned in the staple cavity. The sled is movable from a proximal position to a distal position during a firing stroke. The sled is configured to move the staple driver from an unfired position to a fired position to eject the staple from the staple cavity during the firing stroke. The sled is movable from the distal position toward the proximal position during a retraction stroke. The sled comprises a distal ramp and a proximal ramp. The distal ramp is configured to engage and move the staple driver from an unfired position to a fired position during the firing stroke. The proximal ramp configured to engage and move a the staple driver toward the fired position during the retraction stroke. The proximal ramp is oriented at a first angle relative to the longitudinal axis during the firing stroke. The proximal ramp is oriented at a second angle relative to the longitudinal axis during the retraction stroke. The second angle is different than the first angle.

Example 34—The staple cartridge of Example 33, wherein the second angle is smaller than the first angle.

Example 35—The staple cartridge of Examples 33 or 34, wherein the sled comprises a knife movable within the longitudinal slot.

The entire disclosures of U.S. Pat. No. 11,589,865, entitled METHODS FOR CONTROLLING A POWERED SURGICAL STAPLER THAT HAS SEPARATE ROTARY CLOSURE AND FIRING SYSTEMS, which issued on Feb. 28, 2023, U.S. Pat. No. 6,978,921, entitled SURGICAL STAPLING INSTRUMENT INCORPORATING AN E-BEAM FIRING MECHANISM, which issued on Dec. 27, 2005, U.S. Pat. No. 10,213,203, entitled STAPLE CARTRIDGE ASSEMBLY WITHOUT A BOTTOM COVER, which issued on Feb. 26, 2019, U.S. Pat. No. 10,945,727, entitled STAPLE CARTRIDGE WITH DEFORMABLE DRIVER RETENTION FEATURES, which issued on Mar. 16, 2021, U.S. Pat. No. 11,234,698, entitled STAPLING SYSTEM COMPRISING A CLAMP LOCKOUT AND A FIRING LOCKOUT, which issued on Feb. 1, 2022, U.S. Pat. No. 11,540,826, entitled SURGICAL STAPLER END EFFECTOR SLED HAVING CARTRIDGE WALL SUPPORT FEATURE, which issued on Jan. 3, 2023, U.S. Pat. No. 10,299,792, entitled FASTENER CARTRIDGE COMPRISING NON-UNIFORM FASTENERS, which issued on May 28, 2019, U.S. Pat. No. 8,540,133, entitled STAPLE CARTRIDGE, which issued on Sep. 24, 2013, U.S. Pat. No. 9,788,835, entitled DEVICES AND METHODS FOR FACILITATING EJECTION OF SURGICAL FASTENERS FROM CARTRIDGES, which issued on Oct. 17, 2017, U.S. Pat. No. 10,105,142, entitled SURGICAL STAPLER WITH PLURALITY OF CUTTING ELEMENTS, which issued on Oct. 23, 2018, U.S. Pat. No. 10,537,324, entitled STEPPED STAPLE CARTRIDGE WITH ASYMMETRICAL STAPLES, which issued on Jan. 21, 2020, U.S. Pat. No. 7,669,746, entitled STAPLE CARTRIDGES FOR FORMING STAPLES HAVING DIFFERING FORMED STAPLE HEIGHTS, which issued on Mar. 2, 2010, U.S. Pat. No. 8,123,100, entitled SURGICAL STAPLING INSTRUMENTS INCLUDING A CARTRIDGE HAVING MULTIPLE STAPLE SIZES, which issued on Feb. 28, 2012, U.S. Pat. No. 7,407,075, entitled STAPLE CARTRIDGE HAVING MULTIPLE STAPLE SIZES FOR A SURGICAL STAPLING INSTRUMENT, which issued on Aug. 5, 2008, U.S. Pat. No. 10,085,749, entitled SURGICAL APPARATUS WITH CONDUCTOR STRAIN RELIEF, which issued on Oct. 2, 2018, U.S. Pat. No. 10,765,427, entitled METHOD FOR ARTICULATING A SURGICAL INSTRUMENT, which issued on Sep. 8, 2020, U.S. Pat. No. 11,291,445, entitled SURGICAL STAPLE CARTRIDGES WITH INTEGRAL AUTHENTICATION KEYS, which issued on Apr. 5, 2022, U.S. Pat. No. 8,864,007, entitled IMPLANTABLE FASTENER CARTRIDGE HAVING A NON-UNIFORM ARRANGEMENT, which issued on Oct. 21, 2014, U.S. Pat. No. 11,490,890, entitled COMPRESSIBLE NON-FIBROUS ADJUNCTS, which issued on Nov. 8, 2022, U.S. Pat. No. 10,952,724, entitled THREE DIMENSIONAL ADJUNCTS, which issued on Mar. 23, 2021, U.S. Pat. No. 9,770,245, entitled LAYER ARRANGEMENTS FOR SURGICAL STAPLE CARTRIDGES, which issued on Sep. 26, 2017, U.S. Pat. No. 10,123,798, entitled TISSUE THICKNESS COMPENSATOR COMPRISING CONTROLLED RELEASE AND EXPANSION, which issued on Nov. 13, 2018, U.S. Pat. No. 10,166,023, entitled METHOD OF APPLYING A BUTTRESS TO A SURGICAL STAPLER END EFFECTOR, which issued on Jan. 1, 2019, U.S. Pat. No. 11,207,065, entitled METHOD FOR FABRICATING SURGICAL STAPLER ANVILS, which issued on Dec. 28, 2021, U.S. Pat. No. 8,141,762, entitled SURGICAL STAPLER COMPRISING A STAPLE POCKET, which issued on Mar. 27, 2012, U.S. Pat. No. 8,876,857, entitled END EFFECTOR WITH REDUNDANT CLOSING MECHANISMS, which issued on Nov. 4, 2014, U.S. Pat. No. 9,629,631, entitled COMPOSITE DRIVE BEAM FOR SURGICAL STAPLING, which issued on Apr. 25, 2017, U.S. Patent Application Publication No. 2022/0346858, entitled METHOD FOR OPERATING A SURGICAL INSTRUMENT INCLUDING SEGMENTED ELECTRODES, which published on Nov. 3, 2022, U.S. Patent Application Publication No. 2022/0304680, entitled DRIVERS FOR FASTENER CARTRIDGE ASSEMBLIES HAVING ROTARY DRIVE SCREWS, which published on Sep. 29, 2022, U.S. Patent Application Publication No. 2022/0304679, entitled METHOD OF USING A POWERED STAPLING DEVICE, which published on Sep. 29, 2022, U.S. Patent Publication No. 2019/0298350, entitled METHODS FOR CONTROLLING A POWERED SURGICAL STAPLER THAT HAS SEPARATE ROTARY CLOSURE AND FIRING SYSTEMS, which published on Oct. 3, 2019, U.S. Patent Application Publication No. 2017/0367695, entitled STAPLE CARTRIDGE COMPRISING WIRE STAPLES AND STAMPED STAPLES, which published on Dec. 28, 2017, U.S. Patent Application Publication No. 2015/0134077, entitled SEALING MATERIALS FOR USE IN SURGICAL STAPLING, which published on May 14, 2015, U.S. Patent Application Publication No. 2018/0168615, entitled METHOD OF DEFORMING STAPLES FROM TWO DIFFERENT TYPES OF STAPLE CARTRIDGES WITH THE SAME SURGICAL STAPLING INSTRUMENT, which published on Jun. 21, 2018, U.S. Patent Application Publication No. 2018/0132849, entitled STAPLE FORMING POCKET CONFIGURATIONS FOR CIRCULAR SURGICAL STAPLER ANVIL, which published on May 17, 2018, U.S. Patent Application Publication No. 2018/0168613, entitled SURGICAL INSTRUMENTS WITH JAWS THAT ARE PIVOTABLE ABOUT A FIXED AXIS AND INCLUDE SEPARATE AND DISTINCT CLOSURE AND FIRING SYSTEMS, which published on Jun. 21, 2018, U.S. Patent Application Publication No. 2017/0319205, entitled POWERED END EFFECTOR ASSEMBLY WITH PIVOTABLE CHANNEL, which published on Nov. 9, 2017, U.S. Patent Application Publication No. 2014/0001231, entitled FIRING SYSTEM LOCKOUT ARRANGEMENTS FOR SURGICAL INSTRUMENTS, which published on Jan. 2, 2014, U.S. Patent Application Publication No. 2016/0095596, entitled APPARATUS FOR ENDOSCOPIC PROCEDURES, which published on Apr. 7, 2016, U.S. Patent Application Publication No. 2015/0297199, entitled ADAPTER ASSEMBLY WITH GIMBAL FOR INTERCONNECTING ELECTROMECHANICAL SURGICAL DEVICES AND SURGICAL LOADING UNITS, AND SURGICAL SYSTEMS THEREOF, which published on Oct. 22, 2015, U.S. Patent Application Publication No. 2022/0031351, entitled SURGICAL INSTRUMENTS WITH DIFFERENT ARTICULATION JOINT ARRANGEMENTS FOR ACCOMMODATING FLEXIBLE ACTUATORS, which published on Feb. 3, 2022, U.S. Patent Application Publication No. 2022/0031320, entitled SURGICAL INSTRUMENTS WITH FLEXIBLE FIRING MEMBER ACTUATOR CONSTRAINT ARRANGEMENTS, which published on Feb. 3, 2022, U.S. Patent Application Publication No. 2023/0119119, entitled CABLE-DRIVEN ACTUATION SYSTEM FOR ROBOTIC SURGICAL TOOL ATTACHMENT, which published on Apr. 20, 2023, International Patent Publication No. WO2018/071497, entitled STAPLER CARTRIDGE WITH AN INTEGRAL KNIFE, which published on Apr. 18, 2018, International Patent Publication No. WO2018/049211, entitled WRIST ARCHITECTURE, which published on Mar. 15, 2018, U.S. Pat. No. 11,298,129, entitled METHOD FOR PROVIDING AN AUTHENTICATION LOCKOUT IN A SURGICAL STAPLER WITH A REPLACEABLE CARTRIDGE, which issued on Apr. 12, 2022, U.S. Pat. No. 10,898,183, entitled ROBOTIC SURGICAL INSTRUMENT WITH CLOSED LOOP FEEDBACK TECHNIQUES FOR ADVANCEMENT OF CLOSURE MEMBER DURING FIRING, which issued on Jan. 26, 2021, U.S. Pat. No. 5,485,947, entitled LINEAR STAPLING MECHANISM WITH CUTTING MEANS, which issued on Jan. 23, 1996, International Patent Publication No. WO2018/049206, entitled STAPLER RELOAD DETECTION AND IDENTIFICATION, which published on Mar. 15, 2018, U.S. Patent Application Publication No. 2016/0249920, entitled Surgical fastener applying apparatus, which published on Sep. 1, 2016, U.S. Design Patent No. D974,560, entitled STAPLE CARTRIDGE, which issued on Jan. 3, 2023, U.S. Design Pat. No. D967,421, entitled STAPLE CARTRIDGE, which issued on Oct. 18, 2022, U.S. Design Pat. No. D933,220, entitled BUTTRESS ASSEMBLY FOR A SURGICAL STAPLER, which issued on Oct. 12, 2021, U.S. Pat. No. 9,839,420, entitled TISSUE THICKNESS COMPENSATOR COMPRISING AT LEAST ONE MEDICAMENT, which issued on Dec. 12, 2017, U.S. Pat. No. 10,588,623, entitled ADHESIVE FILM LAMINATE, which issued on Mar. 17, 2020, U.S. Pat. No. 8,499,992, entitled DEVICE AND METHOD FOR CONTROLLING COMPRESSION OF TISSUE, which issued on Aug. 6, 2013, U.S. Patent Application Publication No. 2022/0378427, entitled STAPLING INSTRUMENT COMPRISING JAW MOUNTS, which published on Dec. 1, 2022, U.S. Pat. No. 10,349,939, entitled METHOD OF APPLYING A BUTTRESS TO A SURGICAL STAPLER, which issued on Jul. 16, 2019, U.S. Pat. No. 9,386,988, entitled RETAINER ASSEMBLY INCLUDING A TISSUE THICKNESS COMPENSATOR, which issued on Jul. 12, 2016, U.S. Pat. No. 9,072,535, entitled SURGICAL STAPLING INSTRUMENTS WITH ROTATABLE STAPLE DEPLOYMENT ARRANGEMENTS, which issued on Jul. 7, 2015, and U.S. Pat. No. 9,844,369, entitled, SURGICAL END EFFECTORS WITH FIRING ELEMENT MONITORING ARRANGEMENTS, which issued on Dec. 19, 2017 are incorporated by reference herein.

The entire disclosures of:

U.S. Pat. No. 5,403,312, entitled ELECTROSURGICAL HEMOSTATIC DEVICE, which issued on Apr. 4, 1995;

U.S. Pat. No. 7,000,818, entitled SURGICAL STAPLING INSTRUMENT HAVING SEPARATE DISTINCT CLOSING AND FIRING SYSTEMS, which issued on Feb. 21, 2006;

U.S. Pat. No. 7,422,139, entitled MOTOR-DRIVEN SURGICAL CUTTING AND FASTENING INSTRUMENT WITH TACTILE POSITION FEEDBACK, which issued on Sep. 9, 2008;

U.S. Pat. No. 7,464,849, entitled ELECTRO-MECHANICAL SURGICAL INSTRUMENT WITH CLOSURE SYSTEM AND ANVIL ALIGNMENT COMPONENTS, which issued on Dec. 16, 2008;

U.S. Pat. No. 7,670,334, entitled SURGICAL INSTRUMENT HAVING AN ARTICULATING END EFFECTOR, which issued on Mar. 2, 2010;

U.S. Pat. No. 7,753,245, entitled SURGICAL STAPLING INSTRUMENTS, which issued on Jul. 13, 2010;

U.S. Pat. No. 8,393,514, entitled SELECTIVELY ORIENTABLE IMPLANTABLE FASTENER CARTRIDGE, which issued on Mar. 12, 2013;

U.S. patent application Ser. No. 11/343,803, entitled SURGICAL INSTRUMENT HAVING RECORDING CAPABILITIES, now U.S. Pat. No. 7,845,537;

U.S. patent application Ser. No. 12/031,573, entitled SURGICAL CUTTING AND FASTENING INSTRUMENT HAVING RF ELECTRODES, filed Feb. 14, 2008;

U.S. patent application Ser. No. 12/031,873, entitled END EFFECTORS FOR A SURGICAL CUTTING AND STAPLING INSTRUMENT, filed Feb. 15, 2008, now U.S. Pat. No. 7,980,443;

U.S. patent application Ser. No. 12/235,782, entitled MOTOR-DRIVEN SURGICAL CUTTING INSTRUMENT, now U.S. Pat. No. 8,210,411;

U.S. patent application Ser. No. 12/235,972, entitled MOTORIZED SURGICAL INSTRUMENT, now U.S. Pat. No. 9,050,083.

U.S. patent application Ser. No. 12/249,117, entitled POWERED SURGICAL CUTTING AND STAPLING APPARATUS WITH MANUALLY RETRACTABLE FIRING SYSTEM, now U.S. Pat. No. 8,608,045;

U.S. Patent Application Ser. No. 12/647,100, entitled MOTOR-DRIVEN SURGICAL CUTTING INSTRUMENT WITH ELECTRIC ACTUATOR DIRECTIONAL CONTROL ASSEMBLY, filed Dec. 24, 2009, now U.S. Pat. No. 8,220,688;

U.S. patent application Ser. No. 12/893,461, entitled STAPLE CARTRIDGE, filed Sep. 29, 2012, now U.S. Pat. No. 8,733,613;

U.S. patent application Ser. No. 13/036,647, entitled SURGICAL STAPLING INSTRUMENT, filed Feb. 28, 2011, now U.S. Pat. No. 8,561,870;

U.S. patent application Ser. No. 13/118,241, entitled SURGICAL STAPLING INSTRUMENTS WITH ROTATABLE STAPLE DEPLOYMENT ARRANGEMENTS, now U.S. Pat. No. 9,072,535;

U.S. patent application Ser. No. 13/524,049, entitled ARTICULATABLE SURGICAL INSTRUMENT COMPRISING A FIRING DRIVE, filed on Jun. 15, 2012, now U.S. Pat. No. 9,101,358;

U.S. patent application Ser. No. 13/800,025, entitled STAPLE CARTRIDGE TISSUE THICKNESS SENSOR SYSTEM, filed on Mar. 13, 2013, now U.S. Pat. No. 9,345,481;

U.S. patent application Ser. No. 13/800,067, entitled STAPLE CARTRIDGE TISSUE THICKNESS SENSOR SYSTEM, filed on Mar. 13, 2013, now U.S. Patent Application Publication No. 2014/0263552;

U.S. Patent Application Publication No. 2007/0175955, entitled SURGICAL CUTTING AND FASTENING INSTRUMENT WITH CLOSURE TRIGGER LOCKING MECHANISM, filed Jan. 31, 2006; and U.S. Patent Application Publication No. 2010/0264194, entitled SURGICAL STAPLING INSTRUMENT WITH AN ARTICULATABLE END EFFECTOR, filed Apr. 22, 2010, now U.S. Pat. No. 8,308,040, are hereby incorporated by reference herein.

The surgical instrument systems described herein have been described in connection with the deployment and deformation of staples; however, the present disclosure may not be so limited. The present disclosure envisions that fasteners other than staples can be deployed, such as clamps or tacks, for example. Moreover, the present disclosure envisions utilizing any suitable means for sealing tissue. An end effector in accordance with the present disclosure can comprise electrodes configured to heat and seal the tissue. Also, an end effector in accordance with the present disclosure can apply vibrational energy to seal the tissue.

Although various devices have been described herein in connection with certain embodiments, modifications and variations to those embodiments may be implemented. Particular features, structures, or characteristics may be combined in any suitable manner in one or more embodiments. Thus, the particular features, structures, or characteristics illustrated or described in connection with one embodiment may be combined in whole or in part, with the features, structures or characteristics of one or more other embodiments without limitation. Also, where materials are disclosed for certain components, other materials may be used. Furthermore, according to various embodiments, a single component may be replaced by multiple components, and multiple components may be replaced by a single component, to perform a given function or functions. The foregoing description and following claims are intended to cover all such modification and variations.

It is worthy to note that any reference numbers included in the appended claims are used to reference exemplary embodiments/elements described in the present disclosure. Accordingly, any such reference numbers are not meant to limit the scope of the subject matter recited in the appended claims.

The devices disclosed herein can be designed to be disposed of after a single use, or they can be designed to be used multiple times. In either case, however, a device can be reconditioned for reuse after at least one use. Reconditioning can include any combination of the steps including, but not limited to, the disassembly of the device, followed by cleaning or replacement of particular pieces of the device, and subsequent reassembly of the device. In particular, a reconditioning facility and/or surgical team can disassemble a device and, after cleaning and/or replacing particular parts of the device, the device can be reassembled for subsequent use. Those skilled in the art will appreciate that reconditioning of a device can utilize a variety of techniques for disassembly, cleaning/replacement, and reassembly. Use of such techniques, and the resulting reconditioned device, are all within the scope of the present application.

The devices disclosed herein may be processed before surgery. First, a new or used instrument may be obtained and, when necessary, cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, and/or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta radiation, gamma radiation, ethylene oxide, plasma peroxide, and/or steam.

While this invention has been described as having exemplary designs, the present invention may be further modified within the spirit and scope of the disclosure. This application is therefore intended to cover any variations, uses, or adaptations of the invention using its general principles.

What is claimed is:

1. A staple cartridge for use with a surgical instrument, wherein said staple cartridge comprises:
   a cartridge body, comprising:
      a deck including a proximal end and a distal end;
      a longitudinal slot extending from said proximal end toward said distal end; and
      a staple cavity defined in said deck;
   a staple removably stored in said staple cavity;
   a staple driver movably positioned in said staple cavity; and
   a sled movable from a proximal position to a distal position during a firing stroke, wherein said sled is movable from said distal position toward said proximal position during a retraction stroke, and wherein said sled comprises:
      a base;
      a central portion configured to move within said longitudinal slot;
      a first rail positioned on a first side of said central portion, wherein said first rail comprises a first distal-facing ramp;
      a second rail positioned on said first side of said central portion, wherein said second rail comprises a second distal-facing ramp, wherein said first distal-facing ramp and said second distal-facing ramp are configured to engage and move said staple driver from an unfired position to a fired position during said firing stroke; and
      a driver lift cam positioned intermediate said first rail and said second rail, wherein said driver lift cam is configured to engage said staple driver and move said staple driver toward said fired position during said retraction stroke.

2. The staple cartridge of claim 1, wherein said driver lift cam comprises an arcuate protrusion extending upwardly from said base.

3. The staple cartridge of claim 1, wherein said sled comprises a knife movable within said longitudinal slot.

4. The staple cartridge of claim 3, wherein said staple cartridge comprises a proximal knife housing configured to store said knife when said sled is in said proximal position.

5. The staple cartridge of claim 1, wherein said staple driver comprises:
   a staple support configured to support said staple thereon;
   a distal ramp; and
   a distal camming surface.

6. The staple cartridge of claim 5, wherein said driver lift cam of said sled is configured to engage said distal ramp of said staple driver during said retraction stroke to lift said staple driver from said unfired position to an intermediate position, and wherein said intermediate position is intermediate said unfired position and said fired position.

7. The staple cartridge of claim 6, wherein at least one of said first rail and said second rail of said sled comprises a proximal-facing ramp configured to engage said distal camming surface of said staple driver during said retraction stroke to move said staple driver from said intermediate position to said fired position.

8. The staple cartridge of claim 1, wherein said driver lift cam of said sled is configured to lift said staple driver a first distance toward its fired position during said retraction stroke of said sled, and wherein at least one of said first rail and said second rail of said sled comprises a proximal-facing ramp configured to engage said staple driver during said retraction stroke to lift said staple driver a second distance toward said fired position during said retraction stroke of said sled.

9. The staple cartridge of claim 1, wherein said first rail defines a first plane and said second rail defines a second plane, and wherein said driver lift cam is positioned intermediate said first plane and said second plane.

10. The staple cartridge of claim 9, wherein said staple driver comprises:
a staple support configured to support said staple thereon;
a distal ramp on said staple support, wherein said driver lift cam is aligned with said distal ramp; and
a proximal camming surface aligned with said first plane or said second plane.

11. The staple cartridge of claim 10, wherein said distal ramp on said staple driver is not aligned with said first plane or said second plane.

12. A surgical instrument, comprising:
an end effector;
a firing driver movable relative to said end effector from a proximal position to a distal position during a firing stroke and from said distal position to said proximal position during a retraction stroke; and
a staple cartridge seated in said end effector, wherein said staple cartridge comprises:
a cartridge body, comprising:
a deck including a proximal end and a distal end;
a longitudinal slot extending from said proximal end toward said distal end; and
a staple cavity defined in said deck;
a staple removably stored in said staple cavity;
a staple driver movably positioned in said staple cavity; and
a sled movable distally from an unfired position to a fired position by said firing driver during said firing stroke, wherein said sled is movable proximally from said fired position to a returned position by said firing driver during said retraction stroke, and wherein said sled comprises:
a first sled component comprising a distal-facing ramp configured to engage and move said staple driver from an unfired position to a fired position during said firing stroke; and
a second sled component movable relative to said first sled component, wherein said second sled component comprises a proximal-facing ramp, wherein said sled is configurable in a collapsed configuration and an expanded configuration, wherein at least a portion of said proximal-facing ramp is nested within said first sled component when said sled is in said collapsed configuration, wherein said sled is in said collapsed configuration during said firing stroke, wherein said sled is in said expanded configuration during said retraction stroke, wherein at least a portion of said proximal-facing ramp extends proximally relative to said first sled component when said sled is in said expanded configuration, and wherein said proximal-facing ramp is configured to engage and move said staple driver toward said fired position during said retraction stroke.

13. The surgical instrument of claim 12, wherein said returned position of said sled is distal to said unfired position of said sled.

14. The surgical instrument of claim 12, wherein said end effector comprises a lockout opening, and wherein said proximal-facing ramp extends over at least a portion of said lockout opening when said sled is in said returned position.

15. The surgical instrument of claim 14, wherein said firing driver enters said lockout opening upon the completion of said retraction stroke.

16. The surgical instrument of claim 12, wherein said sled comprises a knife movable within said longitudinal slot.

17. The surgical instrument of claim 12, wherein said staple cartridge is replaceable.

18. A staple cartridge for use with a surgical instrument, comprising:
a cartridge body, comprising:
a deck including a proximal end and a distal end;
a longitudinal slot extending from said proximal end toward said distal end, wherein said longitudinal slot defines a longitudinal axis; and
a staple cavity defined in said deck;
a staple removably stored in said staple cavity;
a staple driver movably positioned in said staple cavity; and
a sled movable from a proximal position to a distal position during a firing stroke, wherein said sled is configured to move said staple driver from an unfired position to a fired position to eject said staple from said staple cavity during said firing stroke, wherein said sled is movable from said distal position toward said proximal position during a retraction stroke, and wherein said sled comprises:
a distal ramp configured to engage and move said staple driver from an unfired position to a fired position during said firing stroke; and
a proximal ramp configured to engage and move a said staple driver toward said fired position during said retraction stroke, wherein said proximal ramp is oriented at a first angle relative to said longitudinal axis during said firing stroke, and wherein said proximal ramp is oriented at a second angle relative to said longitudinal axis during said retraction stroke, and wherein said second angle is different than said first angle.

19. The staple cartridge of claim 18, wherein said second angle is smaller than said first angle.

20. The staple cartridge of claim 18, wherein said sled comprises a knife movable within said longitudinal slot.

* * * * *